United States Patent [19]
Li et al.

[11] Patent Number: 5,684,126
[45] Date of Patent: Nov. 4, 1997

[54] EBNERIN: A SECRETED VON EBNER'S GLAND PROTEIN ASSOCIATED WITH TASTE BUDS

[75] Inventors: Xiao-Jiang Li; Solomon H. Snyder, both of Baltimore, Md.

[73] Assignee: The Johns Hopkins University School of Medicine, Baltimore, Md.

[21] Appl. No.: 470,350

[22] Filed: Jun. 6, 1995

[51] Int. Cl.$^6$ .............................. A61K 38/00; C07K 1/00
[52] U.S. Cl. .............................. 530/300; 530/350
[58] Field of Search ...................... 530/300, 350

[56] References Cited

PUBLICATIONS

Wijngaard et al "Members of the novel WC1 gene family differentially expressed on subsets of bovine CD4–CD8–gamma delta T lymphocytes", *J. of Immunology*, vol. 152, pp. 3476–3482, 1 Apr. 1994.

Wijngaard et al "Molecular characterization of the WC1 antigen expressed specifically on bovine CD4–CD8–gamma delta T Lymphocytes", *J. of Immunology*, vol. 149, No. 10, pp. 3273–3277, 15 Nov. 1992.

Li et al "Molecular cloning of ebnerin, a von Edner's gland protein associated with taste buds" *J. of Biological Chemistry*, vol. 270, No. 30, pp. 17674–17679, 28 Jul. 1995.

Primary Examiner—Ardin H. Marschel
Assistant Examiner—Jezia Riley
Attorney, Agent, or Firm—Banner & Witcoff, Ltd.

[57] ABSTRACT

The present invention is directed to a novel von Ebner's gland secreted protein, designated Ebnerin, which is formed in the ducts of von Ebner's gland and secreted into fluid bathing the taste buds contained in the taste papillae. Ebnerin has been identified by isolation of a rat cDNA encoding a novel secreted protein of 1290 amino acids.

6 Claims, 10 Drawing Sheets

```
   1  MCDDSWDIND ANVVCRQLGC GWALSAPGSA QFGQGLGPIV LDDVACRGHE
  51  AYLWSCSHRG WLSHNCGHQE DAGVICSDSQ TSSPTPGWWN PGGTNNDVIY
 101  DTQETTETSQ TSSPTPDWWN HGGTINDVIY DTQETTEGTD SGLAVRLVNG
 151  GDRCRGRVEI LYQGSWGTVC DDSWDINDAN VVCRQLGCGW ALSAPGSAQF
 201  GQGSGSIVLD DVACRGHEAY LWSCSHRGWL SHNCGHQEDA GVICSYSQTS
 251  SPTPDSQTSS PTPGWWNPGG TNNDVSYGPE QTTDATDSGL AVRLVNGGDR
 301  CQGRVEILYQ GSWGTVCDDS WDTKDANVVC RQLVCGWALS APGSAHFGQG
 351  SGSIVLDDVA CTGHEAYLWS CSHRGWLSHN CGHHEDAGVI CSDAQTQSTT
 401  WPDMWPTTTP ETTTDWWTTK YSSSVPTTQF PTIADWWTTP SPEYTCGGLL
 451  TLPYGQFSSP YYPGSYPNNA RCLWKIFVSS MNRVTVVFTD VQLEGGCNYD
 501  YILVFDGPEN NSSLIARVCD GFNGSFTSTQ NFMSVVFITD GSVTRRGFQA
 551  DYYSTPISTS TTSPTTFPIV TDWWTTPSPE YTCGGLLTLP YGQFSSPYYP
 601  GSYPNNARCL WKIFVPSMNR VTVVFTDVQL EGGCNYDYIL CFDGPEYNSS
 651  LIARVCDGSN GSFTSTQNFM SVVFITDGSV TRRGFQADYY STPIRTSTTP
 701  PTTFPIITGN DSSLVLRLVN GTNRCEGRVE ILYRGSWVPC ADDSWDINDA
 751  NVVCRQLGCG SALSAPGNAW FGQGSGLIVL DDVSCSGYES HLWNCRHPGW
 801  LVHNCRHVED AGVICSLPDP TPSPGPVWTS PPPVNYTCGG FLTGLSGQFS
 851  SPYYPGSYPN NARCLWNIEV PNNYRVTVVF RDVQLEGGCN YDYIEIFDGP
 901  HHSSPLIARV CDGAMGSFTS TSNFMSVRFT TDHSVTRRGF RADYYSDFDN
 951  NTTNLLCLSN HMRASVSRSY LQSMGYSSRD LVIPGWNVSY QCQPQITQRE
1001  VIFTIPYTGC GTTKQADNET INYSNFLKAA VSNGIIKRRK DLHIHVSCKM
1051  LQNTWVNTMY ITNNTVEIQE VQYGNFDVNI SFYTSSSFLY PVTSSPYYVD
1101  LDQNLYLQAE VLHSDTSLAL PVDTCVASPH PNDFSSLTYD LIRSGCIRDE
1151  TYQSYSSPSP RITRFKFSSF HFLNRFPSVY LQCKLVVCRA NDVSSRCYRG
1201  CVVRSKRDVG SYQEKVDVVL GPIQLQSPSK EKRSLDLAVA DVEKPASSQE
1251  VYPTAAIFGG VFLALVVAVA AFT LGRKTRT ARGQPPSTKM 1290
```

FIG. 1b

```
   1  MCDDSWDIND ANVVCRQLGC GWALSAPGSA QFGQGLGPIV LDDVACRGHE
  51  AYLWSCSHRG WLSHNCGHQE DAGVICSDSQ TSSPTPGWWN PGGTNNDVIY
 101  DTQETTETSQ TSSPTPDWWN HGGTINDVIY DTQETTEGTD SGLAVRLVNG
 151  GDRCRGRVEI LYQGSWGTVC DDSWDINDAN VVCRQLGCGW ALSAPGSAQF
 201  GQGSGSIVLD DVACRGHEAY LWSCSHRGWL SHNCGHQEDA GVICSYSQTS
 251  SPTPDSQTSS PTPGWWNPGG TNNDVSYGPE QTTDATDSGL AVRLVNGGDR
 301  CQGRVEILYQ GSWGTVCDDS WDTKDANVVC RQLVCGWALS APGSAHFGQG
 351  SGSIVLDDVA CTGHEAYLWS CSHRGWLSHN CGHHEDAGVI CSDAQTQSTT
 401  WPDMWPTTTP ETTTDWWTTK YSSSVPTTQF PTIADWWTTP SPEYTCGGLL
 451  TLPYGQFSSP YYPGSYPNNA RCLWKIFVSS MNRVTVVFTD VQLEGGCNYD
 501  YILVFDGPEN NSSLIARVCD GFNGSFTSTQ NFMSVVFITD GSVTRRGFQA
 551  DYYSTPISTS TTSPTTFPIV TDWWTTPSPE YTCGGLLTLP YGQFSSPYYP
 601  GSYPNNARCL WKIFVPSMNR VTVVFTDVQL EGGCNYDYIL GFDGPEYNSS
 651  LIARVCDGSN GSFTSTQNFM SVVFITDGSV TRRGFQADYY STPIRTSTTP
 701  PTTFPIITGN DSSLVLRLVN GTNRCEGRVE ILYRGSWVPC ADDSWDINDA
 751  NVVCRQLGCG SALSAPGNAW FGQGSGLIVL DDVSCSGYES HLWNCRHPGW
 801  LVHNCRHVED AGVICSLPDP TPSPGPVWTS PPFVNYTCGG FLTGLSGQFS
 851  SPYYPGSYPN NARCLWNIEV PNNYRVTVVF RDVQLEGGCN YDYIEIFDGP
 901  HHSSPLIARV CDGAMGSFTS TSNFMSVRFT TDHSVTRRGF RADYYSDFDN
 951  NTTNLLCLSN HMRASVSRSY LQSMGYSSRD LVIPGWNVSY QCQPQITQRE
1001  VIFTIPYTGC GTTKQADNET INYSNFLKAA VSNGIIKRRK DLHIHVSCKM
1051  LQNTWVNTMY ITNNTVEIQE VQYGNFDVNI SFYTSSSFLY PVTSSPYYVD
1101  LDQNLYLQAE VLHSDTSLAL FVDTCVASPH PNDFSSLTYD LIRSGCIRDE
1151  TYQSYSSPSP RITRFKFSSF HFLNRFPSVY LQCKLVVCRA NDVSSRCYRG
1201  CVVRSKRDVG SYQEKVDVVL GPIQLQSPSK EKRSLDLAVA DVEKPASSQE
1251  VYPTAAIFGG VFLALVVAVA AFT LGRKTRT ARGQPPSTKM 1290
```

FIG. 2a

|  |  |  |  |  |  |  |  |
|---|---|---|---|---|---|---|---|
| VEGP-R1 (1) | GTDSGLAVRL | VNGGDRCRGR | VETLYQGSWG | MCDDSWDIN | DANVVCRQLG | CGWALSAPGS |  |
| VEGP-R2 (138) | ATDSGLAVRL | VNGGDRCQGR | VEILYQGSWG | TVCDDSWDIN | DANVVCRQLG | CGWALSAPGS |  |
| VEGP-R3 (285) | GNDSSLVLRL | VNGTNRCEGR | VEILYRGSWG | TVCDDSWDTK | DANVVCRQLV | CGWALSAPGS |  |
| VEGP-R6 (709) | YCSDSRQLRL | VDGGPCGGR | VEILDQGSWG | PCADDSWDIN | DARVVCRQLG | CGSALSAPGN |  |
| WC1 (901) | TCAENRALRL | VDGGACAGR | VEMLEHGEWG | TICDDDWDLD | DAHVVCRQLG | CGEALNATGS |  |
| CD6 (130) | MQRQSNTVRL | VGGSGPHEGR | VEIFHEGQWG | SVCDDTWDLE | GGLVVCRSLG | CGWAVQALPG |  |
| SCAVR (345) |  |  |  | TVCDDRWELR |  | YKGVQSVHKR |  |

|  |  |  |  |  |  |  |
|---|---|---|---|---|---|---|
| VEGP-R1 | AQFGQGLGPI | VLDDVACRGH | EAYLWSCSHR | GWLSHNCGHQ | EDAGVICSDS | (79) |
| VEGP-R2 | AQFGQGSGSI | VLDDVACRGR | EAYLWSCSHR | GWLSHNCGHQ | EDAGVICSYS | (247) |
| VEGP-R3 | AHFGQGSGSI | VLDDVACTGH | EAYLWSCSHR | GWLSHNCGHH | EDAGVICSDA | (414) |
| VEGP-R6 | AWFGQGSGLI | VLDDVSCSGY | ESHLWNCRHP | GWLVHNCRHV | EDAGVICSLP | (818) |
| WC1 | AHFGAGSGPI | WLDDLNCTGK | ESHVWRCPSR | GWGRHDCRHK | EDAGVICSEF | (1010) |
| CD6 | LHFITPGRGPI | HRDQVNCSGA | EAYLWDCPGL | PGQHYCGHK | EDAGVVCSEH | (238) |
| SCAVR | AYFGKGTGPI | WLNEVFCFGK | ESSIEECRIR | QWGVRACSHD | EDAGVITCTT | (453) |

FIG. 2b

```
BMP-1(308)  AQARKLYKCP  ACGET...D   STGNFSSPEY  PNGVSAHMHC  VWRITSVTPGE
MEPD (177)  AKINKLYNCS  RCSTIID..A  AFGSLKSANY  PRNYSDNTNC  VWLIR.TRSR
R4 (434)    DWWTTPSPEY  TCGGLLT..L  PYGQFSSPYY  PGSYPNNARC  LWKIFVSSMN
R5 (571)    DWWTTPSPEY  TCGGLLT..L  PYGQFSSPYY  PGSYPNNARC  LWKIFVPSMN
R7 (827)    VWTSPPFVNY  TCGGFLT..G  LSGQFSSPYY  PGSYPNNARC  LWNIEVPNNY
PS4E (124)  DAYCYNPHAK  ECGGVFT..D  PKRIFKSPGF  PNEYDDNQIC  YWHIRLKYGQ
ENPR (528)  VPTSPPELPT  DCGGPFELWE  PNTTFTSMNF  PNNYPNDAFC  VWNLNAQKGK

BMP-1       KIILNFTSLD  LYRSRLCWYD  YVEVRDGFWR  KAP.LRGRFC  .GSKLPEPIV
MEPD        KISLHFRDFD  LRRTRGCQGD  YVKVYDGSSK  .E........  .GSQIPTDVV
R4          RVTVVFTDVQ  LE..GGCNYD  YILVFDGP.H  YSPVLMNKTC  DGFNGSFT..
R5          RVTVVFRDVQ  LE..GGCNYD  YIEIFDGP.H  NNSSLIARVC  DGAMGSFT..
R7          RIHLSFLNFD  LEYDPGCLAD  DVHGFVGRYC  HSSPLIARVC  GDELPEDII
PS4E        NIQLHFEEFD  LENIA....D  YVEIRDGE.E  DDSLLAVYT   .GPGVEDVF
ENPR

BMP-1       STDSRLWVEF  RSSSNWVGKG  FFAVYEA     (431)
MEPD        SSSSLMLIEF  VTDGRDTASG  FQATFTS     (300)
R4          STQNFMSVVF  ITDGSVTRRG  FQADYYS     (554)
R5          STQNFMSVVF  ITDGSVTRRG  FQADYYS     (691)
R7          STSNFMSVRF  TTDHSVTRRG  FRADYYS     (947)
PS4E        STGNVMTLKF  LSDASVTAGG  FQIKYVT     (247)
ENPR        STTNRMTVLF  ITNDALIKGG  FKANFTT     (649)
```

FIG. 2c

```
GP-2  (216)  LOPLIDCGAN  EIKVKLDKCL  LGGLGFKEDI  ITYLNDRNCR  GTMKDEPNNW
UROM (332)   LEHRLECGAN  DMKVMLGKCO  LKSLGF.DKV  FMYLSDSRCS  GFNDRDNRDW
F3   (951)   NTTNLLCLSN  HMRAMVSRSY  LOSMGYSSRD  LV IPGWNVS  YOCOPOITQR

*
GP-2         VSTTSPVVAN  DCGNILENNG  TOAIYRNTLS  LATDFITRDF  LVNVNFOCAY
UROM         VSVTPARDG   PCGTVLTRNE  THATYSNTLY  LADEIIIRDL  NIKINFACSY
F3           EVIFTIPYT   GCGITKQADN  ETINYSNFLK  AAVSNGLIKR  RKDLHIHVSC

GP-2         PLDMNVSLOT  ALOPIVSSLN  VDVGGAGEFT  VTMALFODOS  YTHPYEGSKV
UROM         PLDMKVSLKT  ALOPMVSALN  IRVGGTGMFT  VRMALFOTPS  YTOPYOGSSV
F3           KMLONTWVNI  MYITNNTVE.  IOEVOYGNED  VNISFYTSSS  FLYPVTSSPY

*
GP-2         LLPVENILYV  GALLNRGDTS  RFKLLTNCY   ATPSGDRNDI  VKYFITRNRC
UROM         TLSTEAFLYV  GTMLDGGDLS  RFALLMTNCY  ATPSSNATDP  LKYFIIODRC
F3           YVDLDONLYL  QAEVLHSDTS  .LALFVDTCV  ASPHPNDFSS  LTYDLIRSGC

*           *
GP-2         PNORDSTINV  EENGVSSESR  FSVOMFMFAG  NYDLVFLHCE  VYLC  (460)
UROM         PHTRDSTIQV  VENGESSOGR  FSVOMFRFAG  NYDLVLHCE   VYLC  (576)
F3           ..IRDETYQS  YSSPSPRITR  FKFSSFHELN  RFPSVYLOCK  LVVC  (1189)
```

FIG. 6a
FIG. 6b

EBNERIN: A SECRETED VON EBNER'S GLAND PROTEIN ASSOCIATED WITH TASTE BUDS

TECHNICAL FIELD OF THE INVENTION

The present invention is directed to a novel protein secreted by von Ebner's glands.

BACKGROUND OF THE INVENTION

Saliva is the first digestive fluid secreted by the gastrointestinal pathway and performs a variety of functions. It is essential in the formation of small boluses of food, provides lubrication for swallowing and speech, dissolves a number of chemicals in food substances, and provides digestive enzymes such as amylase and lipase (Hamosh & Scow, 1973; Field & Hand, 1987).

About 90% of saliva is produced by three major glands, the parotid, the submaxillary and the sublingual glands whose secretions drain into the oral cavity. Von Ebner's glands (VEG) are unique salivary glands contained within the tongue and which drain directly into the clefts of the circumvallate and foliate papillae which contain the major taste buds. Secretions of von Ebner's gland directly modulate taste perception (Gurkan & Bradley, 1988).

While von Ebner's gland is known to secrete certain proteins, such as lipase, very little is known of the protein composition of the gland's secretions or the molecular mechanisms that may influence taste perception.

SUMMARY OF THE INVENTION

The present invention is directed to a novel von Ebner's gland secreted protein, designated Ebnerin, which is formed in the ducts of von Ebner's gland and secreted into fluid bathing the taste buds contained in the taste papillae. Ebnerin has been identified by isolation of a rat cDNA encoding a novel secreted protein of 1290 amino acids.

The present invention is directed to a substantially pure polypeptide having the sequence shown in or corresponding to SEQ ID NO: 2. The present invention is also directed to a substantially pure polypeptide having a sequence corresponding to SEQ ID NO: 2, the sequence of said polypeptide selected from the group consisting of: SEQ ID NO: 2, muteins of SEQ ID NO: 2, truncations of SEQ ID NO: 2, and fusion proteins thereof.

The present invention is also directed to a DNA molecule comprising a sequence that encodes a polypeptide having a sequence corresponding to SEQ ID NO: 2, the sequence of said polypeptide selected form the group consisting of SEQ ID NO: 2, muteins of SEQ ID NO: 2, truncations of SEQ ID NO: 2, and fusion proteins thereof. Preferably, the DNA molecule is substantially free of other DNA molecules. Preferably the sequence encoding the polypeptide is an intron-free DNA sequence. The present invention is also directed to a cell population transformed with the DNA molecule. The DNA molecule corresponds to SEQ ID NO: 1.

The present invention provides a single stranded DNA molecule comprising at least 20 contiguous nucleotides of a subsequence found in SEQ ID NO: 1 or a DNA sequence complementary thereto.

Another embodiment of the present invention is a method for determining the presence of a polynucleotide encoding a polypeptide which is substantially homologous to a polypeptide according to SEQ ID NO: 2, wherein said polypeptide is secreted from von Ebner's gland. The method comprises providing a sample suspected of comprising said polynucleotide; incubating the sample with a nucleotide probe having a sequence complementary to a single stranded DNA containing at least 20 contiguous nucleotides of a subsequence found in SEQ ID NO: 1, under conditions where said probe will form hybrids with nucleic acids from the sample; and detecting nucleic acid hybrids.

The present invention is also directed to an antibody specifically immuno-reactive with a polypeptide according to SEQ ID NO: 1, wherein said polypeptide is secreted from von Ebner's gland. Preferably the antibody is monoclonal.

The present invention is also directed to a method for determining the presence of Ebnerin in a tissue. The method includes incubating a tissue sample suspected of containing Ebnerin with an antibody which is specifically reactive with a polypeptide according to SEQ ID NO: 1; and detecting the formation of antibody-antigen complexes involving said antibody.

BRIEF DESCRIPTION OF THE DRAWINGS

Structure and deduced amino acid sequence of Ebnerin.

FIG. 1(b) cDNA for Ebnerin isolated from the taste cDNA library encodes 1290 amino acids with 15 N-linked glycosylation sites that are indicated by black dots above. A putative transmembrane domain is underlined Alignment of amino acid sequence of Ebnerin compared to other proteins.

FIG. 2(a) Repeated domains of Ebnerin (R1, R2, R3 and R6) show 72% amino acid sequence identity to the scavenger receptor cysteine rich domain (SRCR) in WC1 (Wijngaard et al., 1992), 64% to CD6 (Aruffo et al., 1991) and 47% to the macrophage scavenger receptor (Kodama et al., 1990).

FIG. 2(b) The repeated domains of R4, R5 and R7 show 30% amino acid identity to bone morphogenetic protein type-1 (BMP-1) (Fukagawa et al., 1994), 32% to metalloendopeptidase (MEPD) (Elaroussi et al., 1994), 33% to serum inducible protein (PS4E) (Feng & Liau, 1993) and 34% to enteropeptidase precursor (ENPR) (Matsushima et al., 1994).

FIG. 2(c) The extracellular region near the transmembrane domain of Ebnerin (F3) shows 12.3% and 22% amino acid identity to the zona pellucida (ZP) region of the glycoprotein in pancreatic secretory granule membranes (GP-2) (Fukuoka et al., 1991) and uromodulin (UROM) (Pennica et al., 1987), respectively. Amino acids in Ebnerin that are identical to other proteins are shaded and conserved cysteine residues are indicated by asterisks above.

Protein (100 mg/lane) extracted from a variety of tissues was separated by electrophoresis on a 4–12% polyacrylamide gel and transferred to a nitrocellulose filter. The blot was incubated with affinity purified antiserum to Ebnerin (1:100) and immunostained proteins were visualized by the ECL method. TE: the front region of tongue epithelium, VEG: von Ebner's gland, sup: supernatant, pellet: membrane preparations of VEG that were separated from supernatant by centrifugation at 30000 g for 30 min. +peptide: VEG pellet preparations was incubated with the antibodies preabsorbed with peptide antigen (20 mg/ml at 4° C. for 24 hr).

Immunohistochemical localization of Ebnerin in rat tongue.

FIG. 6(a) Antibodies (1:200) and FIG. 6(b) Antibodies preabsorbed with peptide antigen (20 mg/ml) were incubated with rat tongue tissue sections containing circumvallate papillae (CV), von Ebner's gland (VEG). Note in (a) the intense immunoreactivity in the VEG, its duct opening (DO), the cleft of CV and the surface of tongue epithelium (TE). Taste buds (TB) are located near the duct openings of VEG. (100X)

Figure 6C:

FIG. 6(c) Higher magnification of CV section immunostained for Ebnerin antibodies. The intense immunoreactivity is in the cleft of CV where taste buds are located. X400.

Figure 6D:

FIG. 6(d) Higher magnification of VEG section immunostained for Ebnerin. Note that intense immunoreactivity is confined to the epithelial cells of secretory ducts (SD) and is absent from secretory acini (SA). X400.

DETAILED DESCRIPTION OF THE PREFERRED EMBODIMENTS

The present invention is directed to a novel von Ebner's gland secreted protein, designated Ebnerin, which is formed in the ducts of von Ebner's gland and secreted into fluid bathing the taste buds contained in the taste papillae. Ebnerin has been identified by isolation of a rat cDNA encoding a novel secretory protein of 1290 amino acids that is specifically expressed in von Ebner's gland (VEG) and secreted onto the tongue surface along the apical region of taste buds in the clefts of circumvallate papillae.

Ebnerin possesses a putative single transmembrane domain at the C-terminus with 17 amino acids in the cytoplasmic area. The extracellular region of Ebnerin contains a number of repeated domains with homology to the scavenger receptor cysteine-rich (SRCR) domain and to a repeated domain of bone-morphogenetic protein-I and other related proteins. Western blot analysis reveals that Ebnerin exists as both particulate and soluble forms. In situ hybridization and immunohistochemistry demonstrate that Ebnerin is located in secretory duct epithelial cells of von Ebner's gland (VEG) and is secreted onto the tongue surface along the apical region of taste buds in the clefts of circumvallate papillae. The unique structure and localization of Ebnerin suggest that it is a binding protein in saliva for regulation of taste sensation.

Ebnerin displays substantial homology to a number of proteins. The greatest homology lies in four repeated domains which correspond to the scavenger receptor cysteine rich (SRCR) domain of a variety of proteins. Some of these proteins are expressed on the surfaces of cells involved in host defense mechanisms of the immune system, such as T cells, B cells and macrophages and exemplified by the macrophage scavenger receptor proteins. Others are secreted and appear to participate in host defense, such as complement factor I C1r and C1s (Journet and Tosi, 1986; Mackinnon et al., 1987), cyclophilin C binding protein (Friedman et al., 1993) or MAC II binding protein (Koths et al., 1993). Members of this family are expressed in a wide range of organisms from mammals to invertebrates. A prominent member of the family is a speract receptor which occurs in sea urchin sperm and binds speract, the sperm activating peptide secreted by eggs and involved in the chemotaxis of sea urchin eggs and sperm (Bleil & Wassarman, 1980; Kinloch et al, 1992; Lepage et al., 1992). The SRCR family resembles the immunoglobulin superfamily of proteins with multiple copies of cysteine rich domains occurring both in secreted and membrane associated proteins. Like other members of the SRCR family, Ebnerin occurs both in a particulate and a secreted form. Presumably the secreted form is derived by proteolytic cleavage close to the transmembrane area, analogous to the secretion of the Alzheimer's precursor protein (Meier-Ruge et al., 1994) or glycosylphosphatidylinositol (GPI)-linked proteins such as uromodulin and GP-2 proteins (Rindler et al., 1990; Fukuoka et al., 1991; Hoops et al., 1991).

Since members of the SRCR family bind proteins and other ligands, it is likely that Ebnerin possesses a similar function. It is unclear whether the SRCR domains would be involved in ligand binding. They do not appear to participate in ligand binding of the macrophage scavenger receptor (Rohrer et al, 1990). However, almost the entire extracellular domain of the speract receptor comprises SRCR domains which presumably mediate binding to speract secreted by eggs (Kinloch et al, 1992; Lepage et al., 1992). Interestingly, the C-terminal region of Ebnerin displays modest homology to the zona pellucida protein which is released by eggs and interacts with the sperm outer membrane. It is unclear whether the coincidence of homology with egg and sperm signaling proteins in the Ebnerin sequence has physiological relevance.

Ebnerin also possesses three repeated domains which display 30–35% amino acid identity to domains that are held in common by bone morphogenetic protein-I (BP-1), complement I receptor and the Drosophila protein Tolloid which determines dorsal-ventral patterning (Wozney et al., 1988; Schimell et al., 1991). The repeated domain that is common to these proteins and Ebnerin is thought to play a role in ligand binding (Schimell et al., 1991). Accordingly, this area of Ebnerin may mediate ligand interactions.

The existence of Ebnerin in both soluble and particulate fractions and its localization to extracellular fluid surrounding taste buds indicates that it is secreted onto the tongue's surface along the clefts of the circumvallate and foliate papillae. Presumably the soluble form of Ebnerin arises by cleavage of its transmembrane domain in analogy to other membrane anchored secretory proteins such as granule secretory proteins and uromodulin (Rindler et al., 1990; Fukuoka et al., 1991; Hoops & Rindler, 1991). The cleavage might occur through glycophosphatidylinositol anchored regions or at a lysine-lysine bond. In such a cleavage the very short cytoplasmic and transmembranes domains would be removed giving rise to a soluble protein whose molecular weight would be indistinguishable from the membrane associated protein, consistent with a similar mobility in Western blots of the particulate and soluble forms of Ebnerin.

The selective localization of Ebnerin in cells of the ducts of VEG but not in the acinar cells, distinguishes Ebnerin from lipase, mucin and other proteins secreted by acinar cells of salivary glands (Hamosh & Scow, 1973; Field & Hand, 1987). Images of Ebnerin at high magnification immunohistochemistry suggest that it may be an aggregated protein or associated with other proteins when secreted.

Ebnerin may primarily bind to soluble proteins or other tastants or preferentially bind directly to surface proteins of the taste buds. Secretion of growth hormone has been established for parotid and submaxillary salivary glands, (Amano et al., 1993; Humphreys-beher et al., 1994), but has not been investigated for VEG. The structural similarity of Ebnerin to binding proteins for growth hormone such as BMP-1 (Fukagawa et al., 1994) and TGF-β receptor III (Lopez-Casillas, 1991; Wang et al., 1991; Moren et al., 1992) suggests that it might serve as a carrier for putative growth factors produced by VEG.

One protein that might interact with Ebnerin is the von Ebner's gland protein (VEGP) whose sequence resembles that of the odorant binding protein (OBP) (Schmale et al., 1990; Pevsner et al., 1988a). VEGP is also a secretory protein specifically expressed in von Ebner's gland, although its cellular localization and function has not been ascertained. Other members of the lipocalin family of small soluble carrier proteins have been identified (Nagata, 1992). OBP binds a wide range of odorants and is thought to serve as a carrier to deliver them to odorant receptors or possibly to remove odorants from odorant receptors (Pevsner et al., 1985; 1988b, 1990). Conceivably VEGP binds tastants and transports them to or away from taste receptors. It is tempting to suggest that VEGP is a ligand bound by Ebnerin. To investigate such possibility, we examined possible binding of a glutathione-fusion protein for VEGP to $^{35}$S-labeled Ebnerin but have failed to detect direct binding. Despite the absence of direct evidence, participation of Ebnerin in modulating effects of tastants on taste buds would be consistent with studies demonstrating that VEG secretions alter the sensitivity of taste buds to applied tastants (Gurkan & Bradley, 1988). The possible analogy of functions of VEG proteins including VEGP and Ebnerin to similar proteins in olfactory tissues fits with our observations that Ebnerin or an Ebnerin-like transcript is also expressed in olfactory tissues.

In describing the present invention, the following terminology is used in accordance with the definitions set out below.

Two DNA sequences are "substantially homologous" when at least about 85% (preferably at least about 90%, and most preferably at least about 95%) of the nucleotides match over the defined length of the DNA sequences. Sequences that are substantially homologous can be identified in a Southern hybridization experiment under, for example, stringent conditions as defined for that particular system. Defining appropriate hybridization conditions is within the skill of the art. See e.g., Maniatis et al., supra; DNA Cloning, vols. I and II supra; Nucleic Acid Hybridization, supra. Stringent conditions are used for detecting close homologs. Non-stringent conditions are used to detect more distantly related sequences.

A cell has been "transformed" by exogenous DNA when such exogenous DNA has been introduced inside the cell membrane. Exogenous DNA may or may not be integrated (covalently linked) in to chromosomal DNA making up the genome of the cell. Transformed cells can be selected or screened for by standard genetic techniques. A population of transformed cells is generally a pure culture of cells in which all members of the population contain the exogenous DNA. In procaryotes and yeast, for example, the exogenous DNA may be maintained on an episomal element such as a plasmid. With respect to eukaryotic cells, a stably transformed cell is one in which the exogenous DNA has become integrated into a chromosome so that it is inherited by daughter cells through chromosome replication. This stability is demonstrated by the ability of the eukaryotic cell to establish cell lines or clones comprised of a population of daughter cells containing the exogenous DNA.

Polypeptides are polymers made up of a sequence of amino acids linked by peptide bonds, containing at least 10 and usually 50 or more amino acids in the sequence. Proteins are polypeptides which usually have 35 or more amino acids and form a characteristic three dimensional structure (tertiary structure).

One amino acid sequence "corresponds" to another amino acid sequence if at least 75% of the amino acid positions in the first sequence are occupied by the same amino acid residues in the second sequence. Preferably 90% of the amino acid positions are identical, and most preferably 95% of the amino acid positions are identical.

"Conservative amino acid substitutions" are the substitution of one amino acid residue in a sequence by another residue of similar properties, such that the secondary and tertiary structure of the resultant peptides are substantially the same. Conservative amino acid substitutions occur when an amino acid has substantially the same charge as the amino acid for which it is substituted and the substitution has no significant effect on the local conformation of the protein. Amino acid pairs which may be conservatively substituted for one another are well-known to those of ordinary skill in the art.

For the purposes of defining the present invention, two proteins are homologous if 70% of the amino acids in their respective sequences are the same; usually the amino acid sequences of homologous proteins are 80% identical. The sequences of substantially homologous proteins will be 85% identical, preferably the identity will be 90%, most preferably 95%. Two proteins are similar if the majority of the differences between their respective amino acid sequences involve conservative substitutions.

The polypeptides of this invention encompass Ebnerin and Ebnerin analogs. Ebnerin is a naturally occurring, mature protein secreted from von Ebner's gland, and further encompasses all precursors and allelic variations of Ebnerin, as well as including forms of heterogeneous molecular weight that may result from inconsistent processing in vivo. An example of the Ebnerin sequence is shown in FIG. 1. "Ebnerin analogs" are a class of peptides which includes:

1) "Ebnerin muteins," which are polypeptides which are substantially homologous to Ebnerin. Preferably the amino acid sequence of the "mutein" differs from that of Ebnerin by 8 or fewer amino acid residues, more preferably, 7 or fewer residues, even more preferably about 5 or fewer residues and most preferably about 2 or fewer residues. It is sometimes preferred that any differences in the amino acid sequences of the two proteins involve only conservative amino acid substitutions. Alternatively, changes such as the elimination of cysteine which alter the activity or stability of the protein may be preferred.

2) "Truncated Ebnerin peptides," which include fragments of either "Ebnerin" or "Ebnerin muteins" that preferably retain either (i) an amino acid sequence unique to Ebnerin, or (ii) an epitope unique to Ebnerin.

3) "Ebnerin fusion proteins" include heterologous polypeptides which are made up of one of the above polypeptides (Ebnerin, Ebnerin muteins or truncated Ebnerin peptides) fused to any heterologous amino acid sequence. Preferably such heterologous sequences are fused to the N-terminal end of the Ebnerin sequence and comprise a leader sequence to direct secretion.

A composition comprising a selected protein A is "substantially pure" when protein A makes up at least about 75% by weight of the total protein. Preferably, protein A comprises at least about 90% by weight of the total weight, most preferably at least about 99% by weight of the total weight. In the case of a composition comprising a selected biologically active protein, which is substantially free of contaminating proteins, it is sometimes preferred that the composition having the activity of the protein of interest contain species with only a single molecular weight (i.e., a "homogeneous" composition).

As used herein, a "biological sample" refers to a sample of tissue or fluid isolated from a individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, virally infected cells, recombinant cells, and cell components).

"Human tissue" is an aggregate of human cells which may constitute a solid mass. This term also encompasses a suspension of human cells, such as blood cells, or a human cell line.

The term "binding partner" as used herein refers to a molecule capable of binding a ligand molecule with high specificity, as for example an antigen and an antibody specific therefor. In general, the specific binding partners must bind with sufficient affinity to immobilize the analyte copy/complementary strand duplex (in the case of capture probes) under the isolation conditions. Specific binding partners are known in the art, and include, for example, biotin and avidin or streptavidin, IgG and protein A, the numerous known receptor-ligand couples, and complementary polynucleotide strands. In the case of complementary polynucleotide binding partners, the partners are normally at least about 15 bases in length, and may be least 40 bases in length. The polynucleotides may be composed of DNA, RNA, or synthetic nucleotide analogs.

The term "coupled" as used herein refers to attachment by covalent bonds or by strong non-covalent interactions (e.g., hydrophobic interactions, hydrogen bonds, etc.). Covalent bonds may be, for example, ester, ether, phosphoester, amide, peptide, imide, carbon-sulfur bonds, carbon-phosphorus bonds, and the like.

An "epitope" is a structure, usually made up of a short peptide sequence or oligosaccharide, that is specifically recognized or specifically bound by a component of the immune system. T-cell epitopes have generally been shown to be linear oligopeptides. Two epitopes correspond to each other if they can be specifically bound by the same antibody. Two antibodies correspond to each other if both are capable of binding to the same epitope, and binding of one antibody to its epitope prevents binding by the other antibody.

The term "immunoglobulin molecule" encompasses whole antibodies made up of four immunoglobulin peptide chains, two heavy chains and two light chains, as well as immunoglobulin fragments. "Immunoglobulin fragments" are protein molecules related to antibodies, which are known to retain the epitopic binding specificity of the original antibody, such as Fab, F(ab)$'_2$, Fv, etc.

A "single stranded DNA molecule" comprises at least 20 nucleotides which can be used as a hybridization probe for RNA or DNA in or extracted from cells. In the present invention, the nucleotides comprise all or a part of SEQ ID NO: 1 or a DNA sequence complementary thereto. Typically 20 nucleotides will provide a sufficient specificity and uniqueness; however, 25, 30, 35, or 40 contiguous nucleotides of the disclosed sequence, for example, may be desirable for a particular application.

Diagnostic Assays

Detection of sequences cross-reactive with Ebnerin and their expression, may be on the nucleotide or peptide level. Antibodies can be prepared by immunizing mammals with peptides expressed from nucleic acid sequences corresponding to cross-reactive polypeptides, as indicated above, and selecting those antibodies specific to the Ebnerin using techniques that are well known to those skilled in the art. The antibodies may be polyclonal or monoclonal, as is known in the art. These antibodies can detect the presence of cross-reactive protein by a variety of immunoassay techniques. The nucleotide probe sequences provided herein can be used to detect expression of mRNA corresponding to cross-reactive proteins in accordance with any of the standard techniques. Expression may be detected either by in situ hybridization or by extraction and detection of mRNA. The particular procedures for gene probe assays and immunoassays are well-known to those skilled in the art.

General Methods

The practice of the present invention employs, unless otherwise indicated, conventional molecular biology, microbiology, and recombinant DNA techniques within the skill of the art. Such techniques are well known to the skilled worker and are explained fully in the literature. See, e.g., Maniatis, Fritsch & Sambrook, "*Molecular Cloning: A Laboratory Manual*" (1982); "*DNA Cloning: A Practical Approach*," Volumes I and II (D. N. Glover, ed., 1985); "*Oligonucleotide Synthesis*" (M. J. Gait, ed., 1984); "*Nucleic Acid Hybridization*" (B. D. Hames & S. J. Higgins, eds., 1985); "*Transcription and Translation*" (B. D. Hames & S. J. Higgins, eds., 1984); "*Animal Cell Culture*" (R. I. Freshney, ed., 1986); "*Immobilized Cells and Enzymes*" (IRL Press, 1986); B. Perbal, "*A Practical Guide to Molecular Cloning*" (1984), and Sambrook, et al., "*Molecular Cloning: a Laboratory Manual*" (1989).

DNA segments or oligonucleotides having specific sequences can be synthesized chemically or isolated by one of several approaches. The basic strategies for identifying, amplifying and isolating desired DNA sequences as well as assembling them into larger DNA molecules containing the desired sequence domains in the desired order, are well known to those of ordinary skill in the art. See, e.g., Sambrook, et al., (1989); B. Perbal, (1984). Preferably, DNA segments corresponding to Ebnerin may be isolated individually using the polymerase chain reaction (M. A. Innis, et al., "*PCR Protocols: A Guide To Methods and Applications*," Academic Press, 1990). A complete sequence may be assembled from overlapping oligonucleotides prepared by standard methods and assembled into a complete coding sequence. See, e.g., Edge (1981) *Nature* 292:756; Nambair, et al. (1984) *Science* 223:1299; Jay, et al. (1984) *J. Biol. Chem.*, 2.59:6311.

The assembled sequence can be cloned into any suitable vector or replicon and maintained there in a composition which is substantially free of vectors that do not contain the assembled sequence. This provides a reservoir of the assembled sequence, and segments or the entire sequence can be extracted from the reservoir by excising from DNA in the reservoir material with restriction enzymes or by PCR amplification. Numerous cloning vectors are known to those of skill in the art, and the selection of an appropriate cloning vector is a matter of choice (see, e.g., Sambrook, et al., incorporated herein by reference). The construction of vectors containing desired DNA segments linked by appropriate DNA sequences is accomplished by techniques similar to those used to construct the segments. These vectors may be constructed to contain additional DNA segments, such as bacterial origins of replication to make shuttle vectors (for shuttling between prokaryotic hosts and mammalian hosts), etc.

Procedures for construction and expression of mutant proteins of defined sequence are well known in the art. A DNA sequence encoding a mutant form of Ebnerin can be synthesized chemically or prepared from the wild-type sequence by one of several approaches, including primer extension, linker insertion and PCR (see, e.g., Sambrook, et al.). Mutants can be prepared by these techniques having additions, deletions and substitutions in the wild-type sequence. It is preferable to test the mutants to confirm that they are the desired sequence by sequence analysis and/or the assays described below. Mutant protein for testing may be prepared by placing the coding sequence for the polypeptide in a vector under the control of a promoter, so that the DNA sequence is transcribed into RNA and translated into protein in a host cell transformed by this (expression) vector. The mutant protein may be produced by growing host cells transfected by an expression vector containing the coding sequence for the mutant under conditions whereby the polypeptide is expressed. The selection of the appropriate growth conditions is within the skill of the art.

The presence of Ebnerin in a tissue may be determined by incubating a tissue sample suspected of containing Ebnerin with an antibody which is specifically reactive with a polypeptide according to SEQ ID NO: 1 and then detecting the formation of antibody-antigen complexes involving said antibody. Any immunoassay format known in the art may be employed.

EXAMPLES

METHODS

Polymerase Chain Reaction (PCR) and Northern analysis

Circumvallate papillae containing taste buds and tongue epithelium were dissected as previously described (Hwang et al., 1990), and RNA was extracted from the circumvallate papillae. Ten µg total RNA were reverse transcribed using 1 µg of oligo-dT as primer. One µl of the reverse transcription mix was used in a 25 µl PCR reaction containing 1.5 mM $MgCl_2$, 400 nM primers, 200 µM dNTP and 0.5 unit of Taq Polymerase (Boehringer Mannheim). To search for genes associated with salty taste, degenerate primers based on the published sequences of the amiloride sensitive sodium channel (Canessa et al., 1993) were used to amplify mRNA from rat circumvallate papillae. PCR conditions were 35 cycles of 1 min at 95° C., 2 min at 45° C. or 65° C. and 1 min at 72° C. PCR products were then subcloned into Bluescript vector and sequenced. The PCR primers used in this study were the forward primer (GGACAGAATTCGNGGNAA(T/C)TA(T/C)GGNGA(T/C)TG) (SEQ ID NO: 3), and the reverse primer (GATCCACTCGAGNGA(T/C)TTNACNGANGGCCA) (SEQ ID NO: 4), which respectively correspond to $^{372}$SLGGNYGDC$^{380}$ (SEQ ID NO: 5) and $^{520}$WPSVKSQ$^{526}$ (SEQ ID NO: 6) of the amiloride sensitive sodium channel (Canessa et al., 1993). Total RNA (20 µg) was prepared from various rat tissues, fractionated on 1% agarose/formaldehyde gels and blotted onto a nitrocellulose membrane. [$^{32}$P]dCTP labeled PCR product (400 bp) was used as a probe. The blot was hybridized in 50% formamide, 5× SSC hybridization buffer at 42° C. and washed with 0.1× SSC at 65° C. The blot was then exposed to X-ray film for 1 day at −70° C.

Constructing and screening of a rat circumvallate papillae cDNA library.

A rat taste cDNA library was constructed as previously described (Li et al., 1994). Total RNA was extracted from the circumvallate papillae of 500 rats. Poly (A$^+$)RNA was prepared by passing RNA through an oligo-dT column twice. About 5 µg poly (A$^+$)RNA were converted to cDNA for construction of the cDNA library, using a Lambda Zap vector cDNA library synthesis Kit (Stratagene). The library consists of 1.5×10$^6$ independent clones with an average insert size about 1.2 kb. The cDNA clone generated by PCR was labeled using a random primer kit and [$^{32}$P]dCTP, and was used to screen a rat circumvallate papillae cDNA library under high stringency (50% formamide, 5× SSC 42° C. for hybridization and 1× SSC 55° C. for a final wash). Positive clones were purified and cDNA was prepared for restriction mapping and sequence analysis.

In situ hybridization cRNA probes were made for in situ hybridization on rat tongue tissue sections. A PCR clone in a Bluescript vector containing a 400 bp insert was used to generate antisense RNA probes with [$^{33}$P]UTP labeling (NEN). Sense RNA probes provided negative controls. Tissue sections (16 µm) were fixed in 4% paraformaldehyde, rinsed in phosphate buffered saline and digested with 10 µg/ml proteinase K at 37° C. for 30 min. Sections were then rinsed in 0.1M triethanolamine, acetylated in 0.25% acetic anhydride for 10 min, and dehydrated in a graded series of ethanol solutions. Hybridization was performed with 10$^6$ cpm/100 µl of probe in 50% formamide, 10% dextran sulfate, 0.3M $MgCl_2$, 10 mM Tris (pH 8), 1× Denhardt's solution, 0.5 mg/ml tRNA and 10 mM DTT overnight at 55° C. Excess cRNA probe was removed by digestion with RNase A (20 µg/ml) for 30 min and washed at a final stringency of 0.1× SSC at 60° C. for 30 min. Slides were hand-dipped in Kodak NTB2 emulsion, exposed for 3–4 days at 4° C., developed and stained with Giemsa stain (Sigma).

Immunoblot and inununohistochemistry

A peptide corresponding to a partial amino sequences of Ebnerin ($^{929}$FTTDHSVTRRGFRADYYS$^{946}$) (amino acids 929–946 of SEQ ID NO: 2) was synthesized with the addition of a lysine on the N-terminus to facilitate conjugating to bovine serum albumin with glutaraldehyde. More specifically, a solution of 5 mg/ml of the synthetic peptide in PBS was mixed well with carrier protein (BSA) 50 mg and the pH was adjusted to 7.5. An equal volume of glutaraldehyde was slowly added to the peptide/BSA solution with constant agitation and then incubated at room temperature for 1 hour. Glycine was added from a 1M stock in PBS (pH 7.2) to a final concentration of 200 mM. The solution was incubated with stirring for 1 hour. Dialysis was performed on the BSA conjugated peptides against PBS overnight with more than three changes.

The conjugated antigen was injected into rabbits. Rabbits were injected subdermal with 500 μl peptide-BSA (250 mg antigen) +500 μl Freund's Complete Adjuvant. Three weeks later, the rabbits were boosted by injecting subcutaneously 500 μl peptide-BSA and 500 μl Freund's incomplete Adjuvant. The rabbits were reboosted with 250 μl every four weeks. The rabbits were bled ten days after the boosts.

Antisera were purified by an Affi-gel-15 (Bio-Rad) affinity column following standard procedures (Antibodies Lab Manual, 1988). The purified antiserum contains 12 mg/ml antibody. In Western blot analysis 1:100 dilution of purified antiserum were used. Protein samples were prepared from various tissues homogenized in PBS buffer containing proteinase inhibitors (1 mM pepstain A, 0.1 mM aprotinin, 0.1 mM phenylmethylsulfonyl fluoride and 10 mM leupeptin). Protein samples (100 mg) were denatured in SDS sample buffer at 100° C. for 5 min before loading onto a 4–12% gradient SDS gel. Fractionated proteins were transferred onto nitrocellulose membranes and blots were blocked in PBS with 5% non-fat dry milk. Blots were then incubated with 1:200 dilution antibody in the same buffer overnight at 4° C. ECL assay was used to detect stained proteins following instructions from the kit (Amersham).

Tissue sections for immunohistochemical studies were fixed with 4% paraformadehyde at room temperature for 15 min, 0.4% Triton in PBS 30 min and 0.3% $H_2O_2$ in methanol for 15 min with washes in PBS following each treatment. Sections were then blocked in 5% normal goat serum in PBS for 1 hr and incubated with 1:200 diluted antibody in PBS for 24 hr at 4° C. ABC and DAB detecting kits (Vector) were used to visualize immunoreactivity signals in the tissue sections.

RESULTS

Molecular Cloning of Ebnerin

In a search for taste bud associated proteins linked to salty taste perception, PCR analysis was conducted employing primers based on the sequence of the amiloride sensitive sodium channel, which is involved in salty taste perception (Heck et al., 1984; Schiffman et al., 1983). A novel PCR product was identified unrelated to the amiloride-sensitive channel. Initial Northern blots of this PCR product revealed selective enrichment in von Ebner's gland. The PCR product was employed to screen a cDNA library derived from circumvallate papillae containing taste buds and obtained a cDNA of 4267 bp which encodes a protein of 1289 amino acids that is designated Ebnerin (FIG. 1).

Figure 1A:
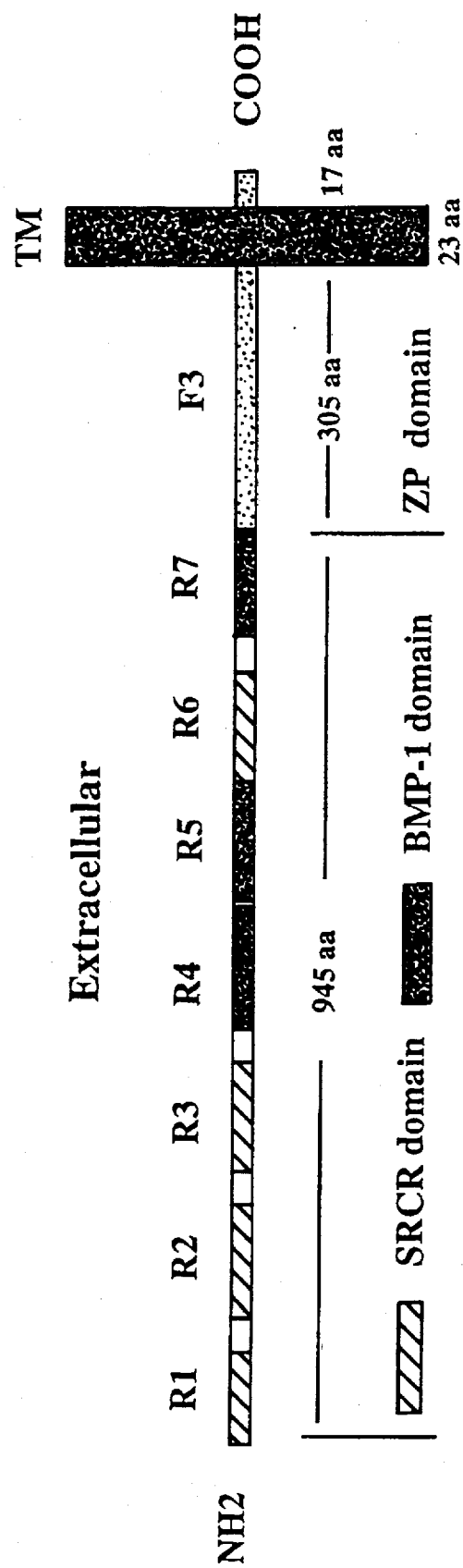
FIG. 1(a) Ebnerin contains a putative transmembrane domain (23 amino acids) and cytoplasmic region of 17 amino acids at the C-terminus. The N-terminus and major portion of Ebnerin are extracellular and contain a number of repeated domains. R1, R2, R3 and R6 represent the repeated domains with sequence similarity to the scavenger receptor cysteine rich domain (SRCR) while R4, R5 and R7 are repeated domains homologous to the repeat domain in bone morphogenetic protein-1 (BMP-1). F3 is a region of Ebnerin that shows homology to the zona pellucida region (ZP) of related proteins.

Ebnerin displays sequence homology to a variety of proteins (FIG. 1A & FIG. 2). It possesses four repeat domains with 50–70% amino acid identity to various members of the scavenger receptor protein family which binds a variety of proteins and peptides (Kodama et al., 1990; Rohrer et al., 1990). There also are three repeat domains with about 30–35% amino acid identity to bone morphogenetic type-I protein (BMP-1) (Fukagawa et al., 1994), TGF-β receptor type III (Lopez-Casillas et al., 1991; Wang et al., 1991; Moren et al., 1992) and related proteins (Wozney et al., 1988; Elaroussi & DeLuca, 1994; Feng & Liau, 1993; Fukagawa et al., 1994). In the C-terminal area of Ebnerin, a 305 amino acid domain displays 12–22% amino acid identity to the zona pellucida (ZP) region in a sperm binding protein of eggs (Lepage et al., 1992) and in uromodulin (UROM) (Pennica et al., 1987) and to the glycoprotein of zymogen granule membranes (Fukuoka et al., 1991). Ebnerin possesses a single 23 amino acid transmembrane region with a very short, 17 amino acid presumed intracellular C-terminal area. There are 15 N-linked glycosylation sites in the putative extracellular domain (FIG. 1B).

Localization of Ebnerin mRNA

Figure 3:
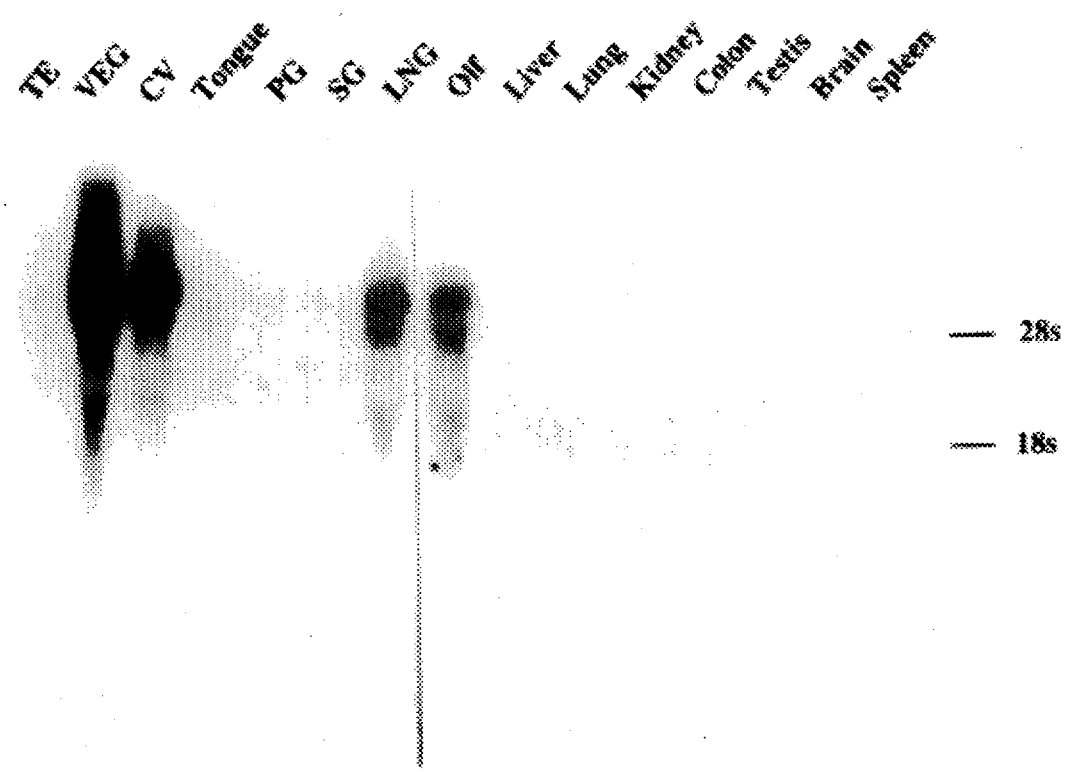
FIG. 3. Tissue distribution of Ebnerin mRNA analyzed by Northern blot. Twenty mg total RNA from various rat tissues were loaded on each lane and hybridized with Ebnerin cDNA probe under high stringency. The blot was exposed to X-ray film for 24 hr. VEG: von Ebner's gland; CV: circumvallate papillae, PG: parotid gland; SG: submaxillary gland, LNG: lateral nasal gland, Olf: olfactory epithelial tissues. An mRNA species of approximately 5 kb was detected in VEG, CV, LNG and Olf.

Northern blot analysis of Ebnerin was conducted in a variety of tissues (FIG. 3). The most prominent expression of Ebnerin mRNA occurs in von Ebner's glands (VEG) with an intense band at about 4.5–5 kb. Circumvallate papillae tissue displays a similarly intense band of the same size. Since circumvallate papillae tissue contains VEG tissue, this band probably derives from contaminating VEG material. Tissue of the olfactory epithelium and the lateral nasal gland displays less intense bands which are slightly smaller than those in VEG. mRNA expression was not detected in any other tissue examined including epithelium from the frontal region of the tongue, tongue tissue that is devoid of VEG, or in parotid gland, submaxillary gland, liver, lung, kidney, colon, testes, brain and spleen.

Figure 4A:
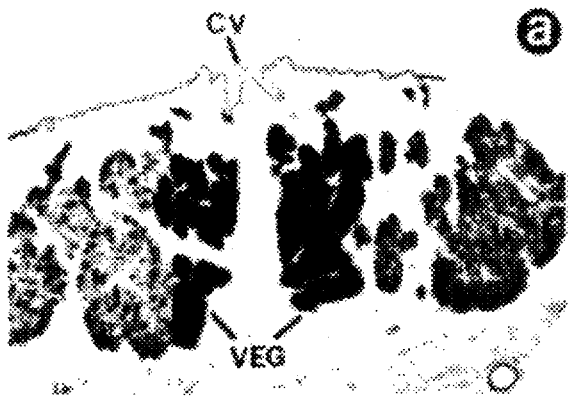
FIG. 4(a) In situ hybridization of $^{33}$P-Ebnerin cRNA probe on tongue in saggital section (10X). Hybridization signals are located in the VEG, von Ebner's gland.
Figure 4B:
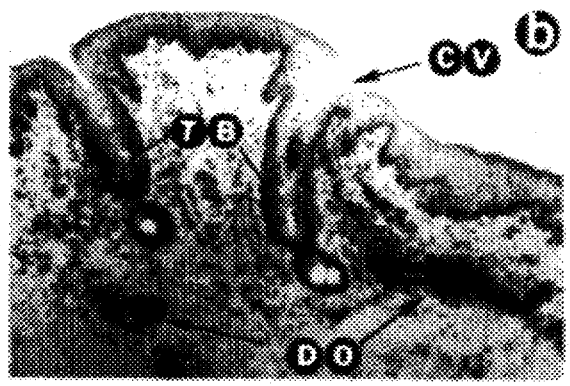
FIG. 4(b) Bright field image of coronal section of circumvallate papillae (200X). TB: taste buds, TE: tongue epithelium, DO: duct opening of von Ebner's gland, VEG: von Ebner's gland.
Figure 4C:
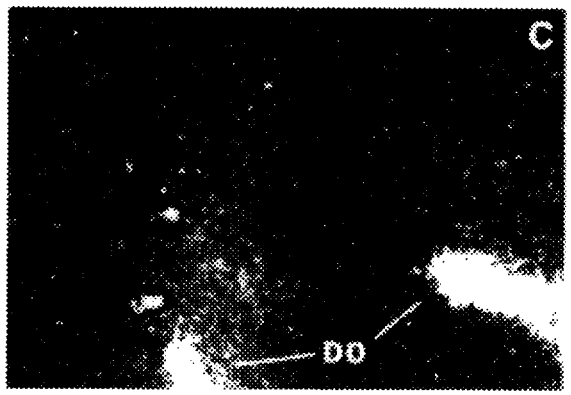
FIG. 4(c) Dark image of same section as in FIG. 4 (b). Note that the hybridization signals are confined to DO in VEG.

In situ hybridization reveals discrete localizations of Ebnerin mRNA (FIG. 4). Autobiographies grains are highly localized to VEG located immediately beneath the circumvallate papillae. Higher power magnification reveals very high levels of grains associated with the openings of the ducts of VEG.

Localization of Ebnerin Protein

Figure 5:
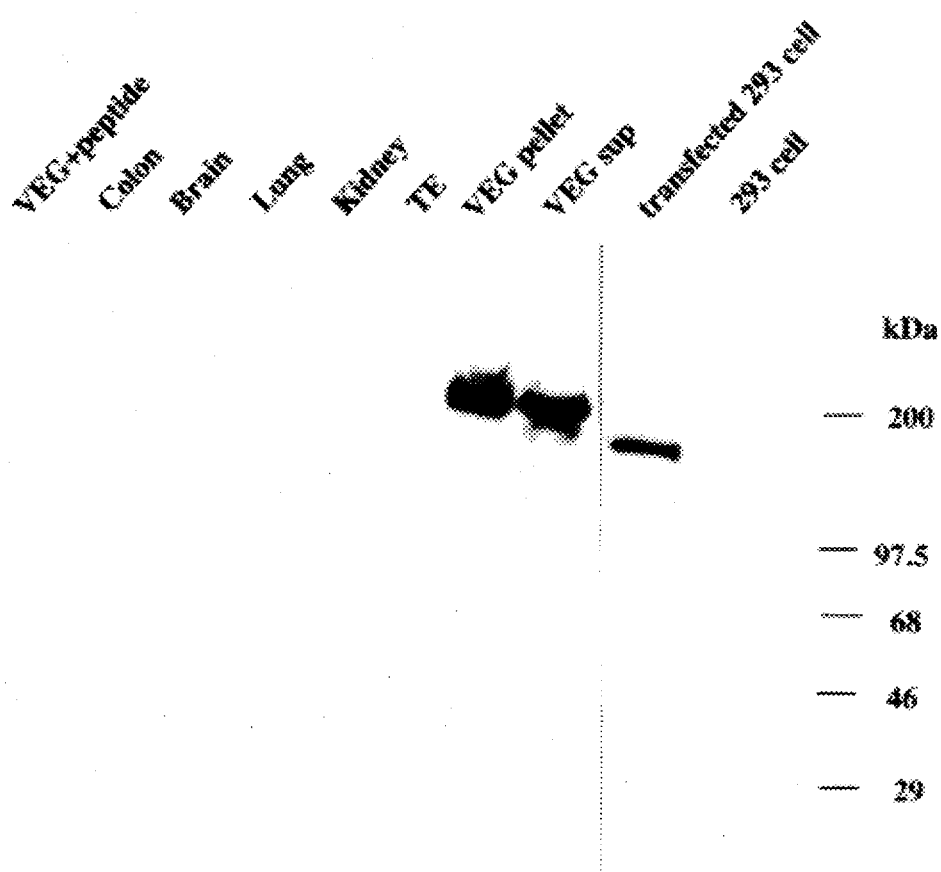
FIG. 5. Western Blot analysis of Ebnerin.

An antiserum was developed to an 18 amino acid peptide in the repeat domain that is homologous to BP-1 protein. Western blot analysis reveals a single immunoreactive band of 210 kDa which occurs with similar intensity in particulate and supernatant preparations of VEG. HEK293 cells transfected with cDNA for Ebnerin display a band of about 170 kDa, while untransfected cells have no immunoreactivity (FIG. 5). The larger size of native Ebnerin than transfected protein could be due to N-glycosylation of protein in VEG or an additional N-terminal peptide not revealed by cDNA cloning. No immunoreactivity was detected in tongue tissue lacking VEG or in kidney, lung, brain, or colon. Preabsorption with the immunizing peptide eliminates immunoreactivity.

Immunohistochemistry with Ebnerin antiserum revealed selective staining associated with VEG (FIG. 6). Staining was also evident in the clefts in apical portions of the circumvallate papillae. Preabsorption with the immunizing peptide abolishes immunoreactivity. High magnification revealed staining selectively localized to the apical region of the taste buds. Staining was also evident at the openings of the ducts of VEG. In the VEG itself intense staining overlied the epithelium of the ducts of the gland, while the acinar tissue did not stain.

REFERENCES

Amano, O., Yoshino, Y., Nishikawa, K. & Iseki, S. (1993) *Cell Tissue Res.* 273, 467–474.

Aruffo, A., Melnick, M. B., Linsley, P. S., Seed, B. (1991) *J. Exp. Med.* 74, 949–52.

Bleil, J. D. & Wassarman, P. M. (1980) *Cell* 20, 873–882.

Canessa, C. M., Horisberger, J. D. & Rossier, B. C. (1993) *Nature* 361, 67–470.

Elaroussi, M. A. & DeLuca, H. F. (1994) *Biochim. Biophys. Acta.* 1217, 1–8.

Feng, P. & Liau, G. (1993) *J. Biol. Chem.* 268, 21453–21457

Field, R. B. & Hand, A. R. (1987) *Am. J. Physiol.* 253, G217–25.

Friedman, J., Trahey, M. & Weissman, I. (1993) *Proc. Natl. Acad. Sci. USA* 90, 6815–6819.

Fukagawa, M., Suzuki, N., Hogan, B. L. & Jones, C. M. (1994) *Dev. Biol.* 163, 175–83.

Fukuoka, S., Freedman, S. D. & Scheele, G. A. (1991) *Proc. Natl. Acad. Sci. USA* 88, 2898–902.

Gurkan, S. & Bradley, R. M. (1988) *Chem. Senses* 13, 655–61.

Hamosh, M., Scow, R. O. (1973) *J. Clin. Invest.* 52, 88–95.

Harlow, E. & Lane, D. (1988) *Antibodies: a laboratory manual.* pp. 313–315, Cold Spring Harbor Laboratory, Cold Spring Harbor, N.Y.

Heck, G. L., Mierson, S. & DeSimone, J. A. (1984) *Science* 223, 403–405.

Hoops, T. C. & Rindler, M. J. (1991) *J. Biol. Chem.* 266, 4257–4236.

Humphreys-beher, M. G., Macauley, S. P., Chegini, N., van Setten, G., Purushotham, K., Stewart, C., Wheeler, T. T. & Schultz, G. S. (1994) *Endocrinology* 134, 963–970.

Hwang, P. M., Verma, A., Bredt, D. S. & Snyder, S. H. (1990) *Proc. Natl. Acad. Sci. USA* 87, 7395–9.

Journet, A. & Tosi, M. (1986) *Biochem. J.* 240, 783–87.

Kinloch, R. A., Roller, R. J., Fimiani, C. M., Wassarman, D. A. & Wassarman, P. M. (1992) *Proc. Natl. Acad. Sci. USA* 85, 6409–13.

Kock, K., Blaker, M. & Schmale, H. (1992) *Cell Tissue Res.* 267, 313–20.

Kodama, T., Freeman, M., Rohrer, L., Zabrecky, J., Matsudaira, P. &

Krieger, M. (1990) *Nature* 343, 531–5.

Koths, K., Taylor, E., Casipit, C. & Wang, A. (1993) *J. Biol. Chem.* 268, 14245–49

Lepage, T. Ghiglione, C. & Gache, C. (1992) *Development* 114, 147–163.

Li, X. J., Blackshaw, S. & Snyder, S. H.(1994) *Proc. Natl. Acad. Sci. USA* 91, 1814–1818.

Lopez-Casillas, F., Cheifetz, S. Doody, J., Andres, J. L., Lane, W. S. &

Massague, J. (1991) *Cell* 67, 785–795.

Mackinnon, C. M., Carter, P. E., Smyth, S. J., Dunbar, B. & Fothergill, J. E. (1987) *Eur. J. Biochem.* 169, 547–53.

Matsushima, M., Ichinose, M., Yahagi, N., Kakei, N., Tsukada, S., Miki, K., Kurokawa, K., Tashiro, K., Shiokawa, K., Shinomiya, K. et al. (1994) *J. Biol. Chem.* 269, 19976–82.

Meier-Ruge, W., Iwangoff, P. & Bertoni-Freddari, C. (1994) *Ann. New York Acad. Sci.* 719, 230–7.

Moren, A. Ichijo, H. & Miyazono, K. (1992) *Biochem. Biophysic. Res. Comm.* 189, 356–362.

Nagata, A. (1992) *Proc. Natl. Acad. Sci. USA* 88, 4020–24.

Pevsner, J., Trifiletti, R. R., Strittmatter, S. M. & Snyder, S. H. (1985) *Proc. Natl. Acad. Sci. USA* 82, 3050–54.

Pennica, D. et al (1987) *Science* 236, 83–88.

Pevsner, J., Reed, R. R., Feinstein, P. G. & Snyder, S. H. (1988a) *Science* 241, 336–339.

Pevsner, J. Hwang, P. M., Sklar, P. B., Venable, J. C. & Snyder, S. H. (1988b) *Proc. Natl. Acad. Sci. USA* 85, 2383–87.

Pevsner, J., Hou, V., Snowman, A. M. & Snyder, S. H. (1990) *J. Biol. Chem.* 265, 6118–6125.

Rindler, M. J., Naik, S. S., Li, N., Hoops, T. C. & Peraldi, M. N. (1990) *J. Biol. Chem.* 265, 20784–9.

Rohrer, L., Freeman, M., Kodama, T., Penman, M. & Krieger-M. (1990) *Nature* 343, 570–2.

Schiffman, S. S., Lockhead, E. & Maes, F. W. (1983) *Proc. Natl. Acad. Sci. USA* 80, 6136–6140.

Schmale, H., Holtgreve, Grez, H. & Christiansen, H., (1990) *Nature* 343, 366–9.

Shimell, M. J., Ferguson, E. L., Childs, S. R. & O'Connor, M. B. (1991) *Cell* 67, 469–481.

Wang, X.-F., Lin, H. Y. Ng-Eaton, E., Downward, J., Lodish, H. F. & Weinberg, R. A. (1991) *Cell* 67, 797–805.

Wijngaard, P. L., Metzelaar, M. J., MacHugh, N. D., Morrison, W. I. & Clevers, H. C. (1992) *J. Immunol.* 149, 3273–7.

Wozney, J. M., Rosen, V., Celeste, A. J., Mitsock, L. M., Whitters, M. J., Kriz, R. W., Hewick, R. M. & Wang, E. A. (1988) *Science* 242, 1528–1534.

---

We claim:

1. A substantially pure polypeptide consisting of the sequence shown in SEQ ID NO: 2.

2. A substantially pure polypeptide encoded by a DNA sequence wherein at least 85% of the DNA sequence matches a DNA sequence which encodes the contiguous amino acid sequence of SEQ ID NO: 2.

3. The polypeptide of claim 2 wherein the sequence of said polypeptide is selected from the group consisting of: SEQ ID NO: 2, muteins of SEQ ID NO: 2, truncations of SEQ ID NO: 2, and fusion proteins thereof.

4. The polypeptide of claim 3 wherein the polypeptide is soluble.

5. The polypeptide of claim 3 which is devoid of the transmembrane region and the cytoplasmic region.

6. The polypeptide of claim 3 which is devoid of the cytoplasmic region.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 4360 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Rattus rattus ( i x ) FEATURE:
        ( A ) NAME/KEY: CDS -continued ( B ) LOCATION: 94..3963

( x i ) SEQUENCE DESCRIPTION: SEQ ID NO:1:

```
GGAACAGATT CTGGTTTGGC TGTGAGGCTG GTGAATGGAG GAGACAGGTG TCGGGGTCGC         60

GTGGAGATCC TTTACCAGGG TTCCTGGGGC ACC ATG TGT GAT GAC AGC TGG GAC        114
                                    Met Cys Asp Asp Ser Trp Asp
                                     1               5

ATC AAT GAT GCC AAC GTG GTG TGC AGG CAG CTG GGC TGT GGC TGG GCC        162
Ile Asn Asp Ala Asn Val Val Cys Arg Gln Leu Gly Cys Gly Trp Ala
         10              15                  20

TTG TCT GCC CCA GGA AGT GCC CAG TTT GGA CAG GGT CTG GGT CCC ATT        210
Leu Ser Ala Pro Gly Ser Ala Gln Phe Gly Gln Gly Leu Gly Pro Ile
     25              30                  35

GTT CTG GAT GAC GTG GCC TGT AGA GGA CAT GAG GCC TAT CTG TGG AGC        258
Val Leu Asp Asp Val Ala Cys Arg Gly His Glu Ala Tyr Leu Trp Ser
 40              45                  50                  55

TGC TCC CAC CGA GGC TGG CTC TCT CAT AAC TGT GGA CAT CAG GAG GAT        306
Cys Ser His Arg Gly Trp Leu Ser His Asn Cys Gly His Gln Glu Asp
             60                  65                  70

GCT GGA GTG ATC TGC TCA GAT TCT CAA ACA AGC AGT CCC ACA CCC GGT        354
Ala Gly Val Ile Cys Ser Asp Ser Gln Thr Ser Ser Pro Thr Pro Gly
                 75                  80                  85

TGG TGG AAC CCC GGG GGC ACA AAT AAC GAT GTG ATC TAC GAC ACT CAA        402
Trp Trp Asn Pro Gly Gly Thr Asn Asn Asp Val Ile Tyr Asp Thr Gln
             90                  95                 100

GAA ACC ACA GAA ACT TCT CAA ACA AGC AGT CCC ACA CCT GAT TGG TGG        450
Glu Thr Thr Glu Thr Ser Gln Thr Ser Ser Pro Thr Pro Asp Trp Trp
        105                 110                 115

AAC CAT GGG GGC ACA ATT AAT GAT GTG ATC TAT GAC ACT CAA GAA ACC        498
Asn His Gly Gly Thr Ile Asn Asp Val Ile Tyr Asp Thr Gln Glu Thr
120                 125                 130                 135

ACA GAA GGA ACA GAT TCT GGT TTG GCT GTG AGG CTG GTG AAT GGA GGA        546
Thr Glu Gly Thr Asp Ser Gly Leu Ala Val Arg Leu Val Asn Gly Gly
                140                 145                 150

GAC AGG TGT CGG GGT CGT GTG GAG ATC CTT TAC CAG GGT TCC TGG GGC        594
Asp Arg Cys Arg Gly Arg Val Glu Ile Leu Tyr Gln Gly Ser Trp Gly
            155                 160                 165

ACC GTG TGT GAC GAC AGC TGG GAC ATC AAT GAT GCC AAC GTG GTG TGC        642
Thr Val Cys Asp Asp Ser Trp Asp Ile Asn Asp Ala Asn Val Val Cys
        170                 175                 180

AGG CAG CTG GGC TGT GGC TGG GCC TTG TCT GCC CCA GGA AGT GCC CAG        690
Arg Gln Leu Gly Cys Gly Trp Ala Leu Ser Ala Pro Gly Ser Ala Gln
185                 190                 195

TTT GGA CAG GGC TCT GGG TCC ATT GTT CTG GAT GAC GTG GCC TGT AGA        738
Phe Gly Gln Gly Ser Gly Ser Ile Val Leu Asp Asp Val Ala Cys Arg
200                 205                 210                 215

GGA CAT GAG GCC TAT CTG TGG AGC TGC TCC CAC CGA GGC TGG CTC TCT        786
Gly His Glu Ala Tyr Leu Trp Ser Cys Ser His Arg Gly Trp Leu Ser
                220                 225                 230

CAT AAC TGT GGA CAT CAG GAG GAT GCT GGA GTC ATC TGT TCA TAT TCT        834
His Asn Cys Gly His Gln Glu Asp Ala Gly Val Ile Cys Ser Tyr Ser
            235                 240                 245

CAA ACA AGC AGT CCC ACA CCC GAT TCT CAA ACA AGC AGT CCC ACA CCC        882
Gln Thr Ser Ser Pro Thr Pro Asp Ser Gln Thr Ser Ser Pro Thr Pro
        250                 255                 260

GGT TGG TGG AAC CCC GGG GGC ACA AAT AAC GAT GTG TCC TAT GGA CCC        930
Gly Trp Trp Asn Pro Gly Gly Thr Asn Asn Asp Val Ser Tyr Gly Pro
    265                 270                 275

GAA CAG ACC ACA GAC GCA ACA GAT TCT GGT TTG GCT GTG AGG CTG GTG        978
Glu Gln Thr Thr Asp Ala Thr Asp Ser Gly Leu Ala Val Arg Leu Val
```

```
      280                     285                           290                           295
AAT  GGA  GGA  GAC  AGG  TGT  CAG  GGT  CGT  GTG  GAG  ATC  CTT  TAC  CAG  GGT           1026
Asn  Gly  Gly  Asp  Arg  Cys  Gln  Gly  Arg  Val  Glu  Ile  Leu  Tyr  Gln  Gly
               300                      305                           310

TCC  TGG  GGT  ACC  GTG  TGT  GAC  GAC  AGC  TGG  GAC  ACC  AAG  GAT  GCC  AAC           1074
Ser  Trp  Gly  Thr  Val  Cys  Asp  Asp  Ser  Trp  Asp  Thr  Lys  Asp  Ala  Asn
               315                      320                           325

GTG  GTG  TGC  AGG  CAG  CTG  GTC  TGT  GGC  TGG  GCC  TTG  TCT  GCC  CCA  GGA           1122
Val  Val  Cys  Arg  Gln  Leu  Val  Cys  Gly  Trp  Ala  Leu  Ser  Ala  Pro  Gly
               330                      335                           340

AGT  GCC  CAC  TTT  GGA  CAA  GGC  TCT  GGA  TCC  ATT  GTT  CTG  GAT  GAC  GTG           1170
Ser  Ala  His  Phe  Gly  Gln  Gly  Ser  Gly  Ser  Ile  Val  Leu  Asp  Asp  Val
               345                      350                           355

GCC  TGT  ACA  GGA  CAT  GAG  GCC  TAT  CTG  TGG  AGC  TGC  TCC  CAC  CGA  GGC           1218
Ala  Cys  Thr  Gly  His  Glu  Ala  Tyr  Leu  Trp  Ser  Cys  Ser  His  Arg  Gly
360                 365                                370                           375

TGG  CTC  TCT  CAT  AAC  TGT  GGC  CAC  CAT  GAG  GAT  GCT  GGA  GTC  ATC  TGT           1266
Trp  Leu  Ser  His  Asn  Cys  Gly  His  His  Glu  Asp  Ala  Gly  Val  Ile  Cys
                    380                      385                           390

TCA  GAT  GCC  CAA  ACC  CAG  AGC  ACA  ACC  TGG  CCA  GAT  ATG  TGG  CCT  ACT           1314
Ser  Asp  Ala  Gln  Thr  Gln  Ser  Thr  Thr  Trp  Pro  Asp  Met  Trp  Pro  Thr
               395                      400                           405

ACC  ACT  CCA  GAA  ACT  ACA  ACA  GAT  TGG  TGG  ACT  ACA  AAA  TAT  TCT  TCC           1362
Thr  Thr  Pro  Glu  Thr  Thr  Thr  Asp  Trp  Trp  Thr  Thr  Lys  Tyr  Ser  Ser
               410                      415                           420

TCT  GTT  CCT  ACA  ACA  CAA  TTC  CCC  ACC  ATA  GCC  GAT  TGG  TGG  ACA  ACT           1410
Ser  Val  Pro  Thr  Thr  Gln  Phe  Pro  Thr  Ile  Ala  Asp  Trp  Trp  Thr  Thr
               425                      430                           435

CCT  TCT  CCG  GAA  TAC  ACC  TGT  GGA  GGT  TTA  CTG  ACC  CTA  CCC  TAT  GGG           1458
Pro  Ser  Pro  Glu  Tyr  Thr  Cys  Gly  Gly  Leu  Leu  Thr  Leu  Pro  Tyr  Gly
440                 445                                450                           455

CAG  TTT  TCC  AGC  CCA  TAC  TAC  CCT  GGA  AGC  TAT  CCT  AAC  AAT  GCC  AGA           1506
Gln  Phe  Ser  Ser  Pro  Tyr  Tyr  Pro  Gly  Ser  Tyr  Pro  Asn  Asn  Ala  Arg
               460                      465                           470

TGT  TTG  TGG  AAA  ATT  TTC  GTC  TCC  AGC  ATG  AAC  CGT  GTG  ACA  GTG  GTC           1554
Cys  Leu  Trp  Lys  Ile  Phe  Val  Ser  Ser  Met  Asn  Arg  Val  Thr  Val  Val
               475                      480                           485

TTC  ACA  GAT  GTG  CAG  CTT  GAA  GGA  GGT  TGC  AAC  TAT  GAC  TAC  ATC  CTG           1602
Phe  Thr  Asp  Val  Gln  Leu  Glu  Gly  Gly  Cys  Asn  Tyr  Asp  Tyr  Ile  Leu
               490                      495                           500

GTT  TTT  GAT  GGC  CCT  GAA  AAC  AAT  TCT  TCT  CTC  ATT  GCT  CGG  GTT  TGT           1650
Val  Phe  Asp  Gly  Pro  Glu  Asn  Asn  Ser  Ser  Leu  Ile  Ala  Arg  Val  Cys
505                 510                                515

GAT  GGG  TTC  AAT  GGA  TCT  TTC  ACC  TCA  ACC  CAG  AAC  TTC  ATG  TCT  GTA           1698
Asp  Gly  Phe  Asn  Gly  Ser  Phe  Thr  Ser  Thr  Gln  Asn  Phe  Met  Ser  Val
520                 525                                530                           535

GTC  TTT  ATC  ACG  GAT  GGC  AGT  GTC  ACG  AGG  AGA  GGG  TTC  CAA  GCT  GAC           1746
Val  Phe  Ile  Thr  Asp  Gly  Ser  Val  Thr  Arg  Arg  Gly  Phe  Gln  Ala  Asp
               540                      545                           550

TAC  TAC  TCC  ACT  CCT  ATC  AGC  ACC  AGC  ACA  ACC  TCT  CCA  ACG  ACG  TTC           1794
Tyr  Tyr  Ser  Thr  Pro  Ile  Ser  Thr  Ser  Thr  Thr  Ser  Pro  Thr  Thr  Phe
               555                      560                           565

CCG  ATC  GTT  ACT  GAT  TGG  TGG  ACA  ACT  CCT  TCT  CCG  GAA  TAC  ACC  TGT           1842
Pro  Ile  Val  Thr  Asp  Trp  Trp  Thr  Thr  Pro  Ser  Pro  Glu  Tyr  Thr  Cys
               570                      575                           580

GGA  GGT  TTA  CTG  ACC  CTA  CCC  TAT  GGG  CAG  TTT  TCC  AGC  CCA  TAC  TAC           1890
Gly  Gly  Leu  Leu  Thr  Leu  Pro  Tyr  Gly  Gln  Phe  Ser  Ser  Pro  Tyr  Tyr
585                                590                           595

CCT  GGA  AGC  TAT  CCT  AAC  AAT  GCC  AGA  TGT  TTG  TGG  AAA  ATT  TTC  GTC           1938
Pro  Gly  Ser  Tyr  Pro  Asn  Asn  Ala  Arg  Cys  Leu  Trp  Lys  Ile  Phe  Val
```

| | | | | | | | | | | | | | | | | |
|---|---|---|---|---|---|---|---|---|---|---|---|---|---|---|---|---|
| 600 | | | | | 605 | | | | | 610 | | | | | 615 | |
| CCC | AGC | ATG | AAC | CGT | GTG | ACA | GTG | GTC | TTC | ACA | GAT | GTG | CAG | CTT | GAA | 1986 |
| Pro | Ser | Met | Asn | Arg 620 | Val | Thr | Val | Val | Phe 625 | Thr | Asp | Val | Gln | Leu 630 | Glu | |
| GGA | GGT | TGC | AAC | TAT | GAC | TAC | ATC | CTG | GGT | TTT | GAT | GGT | CCT | GAA | TAC | 2034 |
| Gly | Gly | Cys | Asn 635 | Tyr | Asp | Tyr | Ile | Leu 640 | Gly | Phe | Asp | Gly | Pro 645 | Glu | Tyr | |
| AAT | TCT | TCT | CTC | ATT | GCT | CGG | GTT | TGT | GAT | GGG | TCC | AAT | GGA | TCT | TTC | 2082 |
| Asn | Ser | Ser 650 | Leu | Ile | Ala | Arg | Val 655 | Cys | Asp | Gly | Ser | Asn 660 | Gly | Ser | Phe | |
| ACC | TCA | ACC | CAG | AAC | TTC | ATG | TCT | GTA | GTC | TTT | ATC | ACG | GAT | GGC | AGT | 2130 |
| Thr | Ser 665 | Thr | Gln | Asn | Phe | Met 670 | Ser | Val | Val | Phe | Ile 675 | Thr | Asp | Gly | Ser | |
| GTC | ACG | AGG | AGA | GGG | TTC | CAA | GCT | GAC | TAC | TAC | TCC | ACT | CCT | ATC | AGG | 2178 |
| Val 680 | Thr | Arg | Arg | Gly | Phe 685 | Gln | Ala | Asp | Tyr 690 | Tyr | Ser | Thr | Pro | Ile 695 | Arg | |
| ACC | AGC | ACA | ACT | CCT | CCA | ACG | ACG | TTC | CCG | ATC | ATT | ACT | GGA | AAT | GAT | 2226 |
| Thr | Ser | Thr | Thr | Pro 700 | Pro | Thr | Thr | Phe | Pro 705 | Ile | Ile | Thr | Gly | Asn 710 | Asp | |
| TCT | TCA | TTG | GTG | CTG | AGG | CTG | GTA | AAT | GGA | ACA | AAC | CGG | TGT | GAG | GGC | 2274 |
| Ser | Ser | Leu | Val 715 | Leu | Arg | Leu | Val | Asn 720 | Gly | Thr | Asn | Arg | Cys 725 | Glu | Gly | |
| CGA | GTG | GAG | ATC | TTG | TAC | AGA | GGC | TCT | TGG | GTA | CCG | TGT | GCC | GAC | GAC | 2322 |
| Arg | Val | Glu 730 | Ile | Leu | Tyr | Arg | Gly 735 | Ser | Trp | Val | Pro | Cys 740 | Ala | Asp | Asp | |
| AGC | TGG | GAC | ATC | AAT | GAT | GCC | AAT | GTG | GTC | TGC | AGA | CAG | CTC | GGT | TGT | 2370 |
| Ser | Trp 745 | Asp | Ile | Asn | Asp | Ala 750 | Asn | Val | Val | Cys | Arg 755 | Gln | Leu | Gly | Cys | |
| GGC | TCT | GCT | CTG | TCT | GCT | CCA | GGA | AAT | GCT | TGG | TTT | GGT | CAG | GGT | TCA | 2418 |
| Gly 760 | Ser | Ala | Leu | Ser | Ala 765 | Pro | Gly | Asn | Ala | Trp 770 | Phe | Gly | Gln | Gly | Ser 775 | |
| GGG | CTC | ATT | GTC | CTG | GAT | GAT | GTG | TCT | TGC | TCT | GGG | TAT | GAG | TCC | CAC | 2466 |
| Gly | Leu | Ile | Val | Leu 780 | Asp | Asp | Val | Ser | Cys 785 | Ser | Gly | Tyr | Glu | Ser 790 | His | |
| CTG | TGG | AAT | TGT | CGT | CAC | CCT | GGC | TGG | CTT | GTT | CAT | AAT | TGT | CGT | CAT | 2514 |
| Leu | Trp | Asn | Cys 795 | Arg | His | Pro | Gly | Trp 800 | Leu | Val | His | Asn | Cys 805 | Arg | His | |
| GTT | GAG | GAT | GCA | GGA | GTC | ATT | TGC | TCA | CTC | CCT | GAT | CCG | ACT | CCC | TCT | 2562 |
| Val | Glu | Asp 810 | Ala | Gly | Val | Ile | Cys 815 | Ser | Leu | Pro | Asp | Pro 820 | Thr | Pro | Ser | |
| CCT | GGT | CCA | GTT | TGG | ACA | AGT | CCT | CCT | TTT | GTA | AAC | TAT | ACT | TGT | GGA | 2610 |
| Pro | Gly 825 | Pro | Val | Trp | Thr | Ser 830 | Pro | Pro | Phe | Val | Asn 835 | Tyr | Thr | Cys | Gly | |
| GGT | TTC | CTG | ACT | GGA | CTC | TCT | GGG | CAA | TTT | TCT | AGC | CCA | TAC | TAC | CCT | 2658 |
| Gly | Phe | Leu | Thr | Gly 840 | Leu | Ser | Gly | Gln | Phe 845 | Ser | Ser | Pro | Tyr | Tyr 850 | Pro | |
| GGG | AGC | TAT | CCT | AAT | AAT | GCC | AGA | TGT | TTG | TGG | AAC | ATT | GAA | GTC | CCA | 2706 |
| Gly | Ser | Tyr | Pro | Asn 860 | Asn | Ala | Arg | Cys | Leu 865 | Trp | Asn | Ile | Glu | Val 870 | Pro | |
| AAC | AAC | TAC | CGC | GTG | ACT | GTG | GTC | TTC | AGA | GAT | GTG | CAG | CTG | GAA | GGG | 2754 |
| Asn | Asn | Tyr | Arg 875 | Val | Thr | Val | Val | Phe 880 | Arg | Asp | Val | Gln | Leu 885 | Glu | Gly | |
| GGC | TGC | AAC | TAT | GAC | TAT | ATA | GAG | ATT | TTT | GAT | GGC | CCC | CAC | CAC | AGT | 2802 |
| Gly | Cys | Asn 890 | Tyr | Asp | Tyr | Ile | Glu 895 | Ile | Phe | Asp | Gly | Pro 900 | His | His | Ser | |
| TCA | CCT | CTC | ATT | GCC | CGG | GTT | TGT | GAT | GGG | GCC | ATG | GGC | TCT | TTC | ACT | 2850 |
| Ser | Pro 905 | Leu | Ile | Ala | Arg | Val 910 | Cys | Asp | Gly | Ala | Met 915 | Gly | Ser | Phe | Thr | |
| TCA | ACA | TCC | AAC | TTC | ATG | TCA | GTT | CGC | TTC | ACC | ACT | GAT | CAC | AGT | GTT | 2898 |
| Ser | Thr | Ser | Asn | Phe | Met | Ser | Val | Arg | Phe | Thr | Thr | Asp | His | Ser | Val | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 920 |     |     |     |     | 925 |     |     |     |     | 930 |     |     |     |     | 935 |      |
| ACT | CGA | AGA | GGG | TTC | CGG | GCT | GAC | TAC | TAC | TCA | GAC | TTT | GAC | AAT | AAT | 2946 |
| Thr | Arg | Arg | Gly | Phe | Arg | Ala | Asp | Tyr | Tyr | Ser | Asp | Phe | Asp | Asn | Asn |      |
|     |     |     | 940 |     |     |     |     | 945 |     |     |     |     | 950 |     |     |      |
| ACC | ACC | AAT | CTC | CTT | TGT | CTG | TCA | AAT | CAC | ATG | AGA | GCC | AGT | GTG | AGC | 2994 |
| Thr | Thr | Asn | Leu | Leu | Cys | Leu | Ser | Asn | His | Met | Arg | Ala | Ser | Val | Ser |      |
|     |     |     | 955 |     |     |     |     | 960 |     |     |     |     | 965 |     |     |      |
| AGG | AGC | TAC | CTT | CAG | TCC | ATG | GGC | TAC | TCC | TCC | AGG | GAT | CTT | GTC | ATT | 3042 |
| Arg | Ser | Tyr | Leu | Gln | Ser | Met | Gly | Tyr | Ser | Ser | Arg | Asp | Leu | Val | Ile |      |
|     |     |     | 970 |     |     |     |     | 975 |     |     |     |     | 980 |     |     |      |
| CCT | GGT | TGG | AAC | GTG | AGT | TAC | CAG | TGT | CAG | CCT | CAG | ATA | ACA | CAA | AGG | 3090 |
| Pro | Gly | Trp | Asn | Val | Ser | Tyr | Gln | Cys | Gln | Pro | Gln | Ile | Thr | Gln | Arg |      |
|     |     |     | 985 |     |     |     |     | 990 |     |     |     |     | 995 |     |     |      |
| GAG | GTC | ATA | TTC | ACA | ATT | CCC | TAC | ACA | GGC | TGC | GGT | ACT | ACC | AAA | CAG | 3138 |
| Glu | Val | Ile | Phe | Thr | Ile | Pro | Tyr | Thr | Gly | Cys | Gly | Thr | Thr | Lys | Gln |      |
| 1000|     |     |     |     | 1005|     |     |     |     | 1010|     |     |     |     | 1015|      |
| GCT | GAC | AAC | GAG | ACC | ATC | AAC | TAC | TCC | AAC | TTC | CTC | AAA | GCG | GCT | GTT | 3186 |
| Ala | Asp | Asn | Glu | Thr | Ile | Asn | Tyr | Ser | Asn | Phe | Leu | Lys | Ala | Ala | Val |      |
|     |     |     |     | 1020|     |     |     |     | 1025|     |     |     |     | 1030|     |      |
| TCA | AAT | GGC | ATC | ATC | AAA | AGG | AGA | AAG | GAT | CTC | CAC | ATC | CAT | GTC | AGC | 3234 |
| Ser | Asn | Gly | Ile | Ile | Lys | Arg | Arg | Lys | Asp | Leu | His | Ile | His | Val | Ser |      |
|     |     |     |     | 1035|     |     |     |     | 1040|     |     |     |     | 1045|     |      |
| TGC | AAG | ATG | CTT | CAG | AAC | ACC | TGG | GTC | AAC | ACC | ATG | TAC | ATC | ACC | AAC | 3282 |
| Cys | Lys | Met | Leu | Gln | Asn | Thr | Trp | Val | Asn | Thr | Met | Tyr | Ile | Thr | Asn |      |
|     |     |     |     | 1050|     |     |     |     | 1055|     |     |     |     | 1060|     |      |
| AAC | ACA | GTC | GAG | ATC | CAG | GAA | GTC | CAG | TAT | GGC | AAT | TTT | GAC | GTG | AAT | 3330 |
| Asn | Thr | Val | Glu | Ile | Gln | Glu | Val | Gln | Tyr | Gly | Asn | Phe | Asp | Val | Asn |      |
|     |     |     |     | 1065|     |     |     |     | 1070|     |     |     |     | 1075|     |      |
| ATT | TCC | TTT | TAT | ACA | TCC | TCC | TCC | TTG | TAT | CCA | GTG | ACC | AGC | AGC | | 3378 |
| Ile | Ser | Phe | Tyr | Thr | Ser | Ser | Ser | Phe | Leu | Tyr | Pro | Val | Thr | Ser | Ser |      |
| 1080|     |     |     |     | 1085|     |     |     |     | 1090|     |     |     |     | 1095|      |
| CCA | TAT | TAT | GTG | GAT | CTG | GAC | CAG | AAT | TTG | TAC | CTT | CAG | GCC | GAA | GTC | 3426 |
| Pro | Tyr | Tyr | Val | Asp | Leu | Asp | Gln | Asn | Leu | Tyr | Leu | Gln | Ala | Glu | Val |      |
|     |     |     |     | 1100|     |     |     |     | 1105|     |     |     |     | 1110|     |      |
| CTC | CAT | TCG | GAT | ACC | TCT | TTG | GCT | CTG | TTT | GTG | GAC | ACC | TGT | GTG | GCT | 3474 |
| Leu | His | Ser | Asp | Thr | Ser | Leu | Ala | Leu | Phe | Val | Asp | Thr | Cys | Val | Ala |      |
|     |     |     |     | 1115|     |     |     |     | 1120|     |     |     |     | 1125|     |      |
| TCG | CCA | CAT | CCC | AAT | GAC | TTC | TCG | TCT | TTG | ACA | TAT | GAT | CTC | ATC | AGG | 3522 |
| Ser | Pro | His | Pro | Asn | Asp | Phe | Ser | Ser | Leu | Thr | Tyr | Asp | Leu | Ile | Arg |      |
|     |     |     |     | 1130|     |     |     |     | 1135|     |     |     |     | 1140|     |      |
| AGT | GGA | TGC | ATA | CGA | GAT | GAA | ACT | TAC | CAA | TCT | TAC | TCC | TCG | CCC | TCA | 3570 |
| Ser | Gly | Cys | Ile | Arg | Asp | Glu | Thr | Tyr | Gln | Ser | Tyr | Ser | Ser | Pro | Ser |      |
|     |     |     |     | 1145|     |     |     |     | 1150|     |     |     |     | 1155|     |      |
| CCA | CGC | ATC | ACC | CGC | TTT | AAA | TTC | AGT | TCT | TTC | CAC | TTC | CTG | AAC | CGC | 3618 |
| Pro | Arg | Ile | Thr | Arg | Phe | Lys | Phe | Ser | Ser | Phe | His | Phe | Leu | Asn | Arg |      |
| 1160|     |     |     |     | 1165|     |     |     |     | 1170|     |     |     |     | 1175|      |
| TTC | CCC | TCA | GTA | TAC | CTA | CAG | TGT | AAA | CTG | GTG | GTT | TGT | CGA | GCA | AAC | 3666 |
| Phe | Pro | Ser | Val | Tyr | Leu | Gln | Cys | Lys | Leu | Val | Val | Cys | Arg | Ala | Asn |      |
|     |     |     |     | 1180|     |     |     |     | 1185|     |     |     |     | 1190|     |      |
| GAT | GTC | TCC | TCA | CGG | TGC | TAC | AGA | GGA | TGT | GTA | GTA | AGG | TCC | AAG | AGG | 3714 |
| Asp | Val | Ser | Ser | Arg | Cys | Tyr | Arg | Gly | Cys | Val | Val | Arg | Ser | Lys | Arg |      |
|     |     |     |     | 1195|     |     |     |     | 1200|     |     |     |     | 1205|     |      |
| GAT | GTA | GGC | TCC | TAC | CAA | GAA | AAG | GTG | GAT | GTT | GTT | CTG | GGA | CCC | ATC | 3762 |
| Asp | Val | Gly | Ser | Tyr | Gln | Glu | Lys | Val | Asp | Val | Val | Leu | Gly | Pro | Ile |      |
|     |     |     |     | 1210|     |     |     |     | 1215|     |     |     |     | 1220|     |      |
| CAG | TTG | CAA | TCT | CCC | AGC | AAA | GAA | AAG | AGG | AGT | CTC | GAC | TTG | GCA | GTG | 3810 |
| Gln | Leu | Gln | Ser | Pro | Ser | Lys | Glu | Lys | Arg | Ser | Leu | Asp | Leu | Ala | Val |      |
|     |     |     |     | 1225|     |     |     |     | 1230|     |     |     |     | 1235|     |      |
| GCA | GAT | GTG | GAG | AAG | CCA | GCC | AGC | TCC | CAG | GAG | GTC | TAT | CCC | ACT | GCA | 3858 |
| Ala | Asp | Val | Glu | Lys | Pro | Ala | Ser | Ser | Gln | Glu | Val | Tyr | Pro | Thr | Ala |      |

|  | 1240 |  |  |  | 1245 |  |  |  | 1250 |  |  |  | 1255 |  |  |
|---|---|---|---|---|---|---|---|---|---|---|---|---|---|---|---|
| GCC | ATC | TTT | GGT | GGA | GTC | TTC | CTG | GCC | CTG | GTT | GTA | GCT | GTG | GCA | GCC | 3906 |
| Ala | Ile | Phe | Gly | Gly | Val | Phe | Leu | Ala | Leu | Val | Val | Ala | Val | Ala | Ala |  |
|  |  |  |  | 1260 |  |  |  |  | 1265 |  |  |  |  | 1270 |  |  |
| TTC | ACA | CTG | GGA | AGG | AAG | ACA | CGC | ACT | GCC | CGT | GGT | CAA | CCT | CCA | AGT | 3954 |
| Phe | Thr | Leu | Gly | Arg | Lys | Thr | Arg | Thr | Ala | Arg | Gly | Gln | Pro | Pro | Ser |  |
|  |  |  |  | 1275 |  |  |  |  | 1280 |  |  |  |  | 1285 |  |  |

| ACT | AAG | ATG | TGAAGCAAAA | CAACCCAGAC | ATTGGTCCCA | AATGCATAGA | 4003 |
|---|---|---|---|---|---|---|---|
| Thr | Lys | Met |  |  |  |  |  |
|  |  | 1290 |  |  |  |  |  |

```
TTCCCAGAAA  AGATGGAAGT  CAGGAGTGTC  TAATGCCTGG  CACCCAGATA  CACGATGACT    4063
AGGCTTCCCT  TAGCACAAAT  GTGTGGCCGA  GTATGATCAG  ATGGTAAAGA  AGAAAGGTGG    4123
GGGCCAAGTT  TTCCCAGGGT  CTAGAGGCTG  AAGGCTGGGA  AGAATGTCAT  AGGAGAATGA    4183
GATCAGTGTC  TACAATAACA  GGCAACTGTG  AGCCAAACAT  TGGCATCACC  ATCCTTTCTC    4243
TAGCTAGAAT  TTCCCTTTCC  CCCTTTTATA  CTGACTTTTT  TGAACTGTAG  TGTTAAATGG    4303
ACCTTTCCGT  ACAACAAACT  AAAATAAAGA  ATCTTTTTCC  AAAAAAAAA   AAAAAA        4360
```

( 2 ) INFORMATION FOR SEQ ID NO:2:

( i ) SEQUENCE CHARACTERISTICS:
        ( A ) LENGTH: 1290 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Cys  Asp  Asp  Ser  Trp  Asp  Ile  Asn  Asp  Ala  Asn  Val  Val  Cys  Arg
 1                  5                   10                      15
Gln  Leu  Gly  Cys  Gly  Trp  Ala  Leu  Ser  Ala  Pro  Gly  Ser  Ala  Gln  Phe
            20                  25                      30
Gly  Gln  Gly  Leu  Gly  Pro  Ile  Val  Leu  Asp  Asp  Val  Ala  Cys  Arg  Gly
        35                  40                      45
His  Glu  Ala  Tyr  Leu  Trp  Ser  Cys  Ser  His  Arg  Gly  Trp  Leu  Ser  His
    50                  55                      60
Asn  Cys  Gly  His  Gln  Glu  Asp  Ala  Gly  Val  Ile  Cys  Ser  Asp  Ser  Gln
65                  70                      75                      80
Thr  Ser  Ser  Pro  Thr  Pro  Gly  Trp  Trp  Asn  Pro  Gly  Gly  Thr  Asn  Asn
                85                      90                      95
Asp  Val  Ile  Tyr  Asp  Thr  Gln  Glu  Thr  Thr  Glu  Thr  Ser  Gln  Thr  Ser
                    100                     105                     110
Ser  Pro  Thr  Pro  Asp  Trp  Trp  Asn  His  Gly  Gly  Thr  Ile  Asn  Asp  Val
            115                     120                     125
Ile  Tyr  Asp  Thr  Gln  Glu  Thr  Thr  Glu  Gly  Thr  Asp  Ser  Gly  Leu  Ala
        130                     135                     140
Val  Arg  Leu  Val  Asn  Gly  Gly  Asp  Arg  Cys  Arg  Gly  Arg  Val  Glu  Ile
145                     150                     155                     160
Leu  Tyr  Gln  Gly  Ser  Trp  Gly  Thr  Val  Cys  Asp  Asp  Ser  Trp  Asp  Ile
                    165                     170                     175
Asn  Asp  Ala  Asn  Val  Val  Cys  Arg  Gln  Leu  Gly  Cys  Gly  Trp  Ala  Leu
                180                     185                     190
Ser  Ala  Pro  Gly  Ser  Ala  Gln  Phe  Gly  Gln  Gly  Ser  Gly  Ser  Ile  Val
            195                     200                     205
Leu  Asp  Asp  Val  Ala  Cys  Arg  Gly  His  Glu  Ala  Tyr  Leu  Trp  Ser  Cys
        210                     215                     220
```

-continued

| Ser 225 | His | Arg | Gly | Trp 230 | Leu | Ser | His | Asn | Cys 235 | Gly | His | Gln | Glu | Asp | Ala 240 |
| Gly | Val | Ile | Cys | Ser 245 | Tyr | Ser | Gln | Thr | Ser 250 | Ser | Pro | Thr | Pro | Asp 255 | Ser |
| Gln | Thr | Ser | Ser 260 | Pro | Thr | Pro | Gly | Trp 265 | Trp | Asn | Pro | Gly | Gly 270 | Thr | Asn |
| Asn | Asp | Val 275 | Ser | Tyr | Gly | Pro | Glu 280 | Gln | Thr | Thr | Asp | Ala 285 | Thr | Asp | Ser |
| Gly | Leu 290 | Ala | Val | Arg | Leu | Val 295 | Asn | Gly | Gly | Asp | Arg 300 | Cys | Gln | Gly | Arg |
| Val 305 | Glu | Ile | Leu | Tyr | Gln 310 | Gly | Ser | Trp | Gly | Thr 315 | Val | Cys | Asp | Asp | Ser 320 |
| Trp | Asp | Thr | Lys | Asp 325 | Ala | Asn | Val | Val | Cys 330 | Arg | Gln | Leu | Val | Cys 335 | Gly |
| Trp | Ala | Leu | Ser 340 | Ala | Pro | Gly | Ser | Ala 345 | His | Phe | Gly | Gln | Gly 350 | Ser | Gly |
| Ser | Ile | Val 355 | Leu | Asp | Asp | Val | Ala 360 | Cys | Thr | Gly | His | Glu 365 | Ala | Tyr | Leu |
| Trp | Ser 370 | Cys | Ser | His | Arg | Gly 375 | Trp | Leu | Ser | His | Asn 380 | Cys | Gly | His | His |
| Glu 385 | Asp | Ala | Gly | Val | Ile 390 | Cys | Ser | Asp | Ala | Gln 395 | Thr | Gln | Ser | Thr | Thr 400 |
| Trp | Pro | Asp | Met | Trp 405 | Pro | Thr | Thr | Thr | Pro 410 | Glu | Thr | Thr | Thr | Asp 415 | Trp |
| Trp | Thr | Thr | Lys 420 | Tyr | Ser | Ser | Ser | Val 425 | Pro | Thr | Thr | Gln | Phe 430 | Pro | Thr |
| Ile | Ala | Asp 435 | Trp | Trp | Thr | Thr | Pro 440 | Ser | Pro | Glu | Tyr | Thr 445 | Cys | Gly | Gly |
| Leu | Leu 450 | Thr | Leu | Pro | Tyr | Gly 455 | Gln | Phe | Ser | Ser | Pro 460 | Tyr | Tyr | Pro | Gly |
| Ser 465 | Tyr | Pro | Asn | Asn | Ala 470 | Arg | Cys | Leu | Trp | Lys 475 | Ile | Phe | Val | Ser | Ser 480 |
| Met | Asn | Arg | Val | Thr 485 | Val | Val | Phe | Thr | Asp 490 | Val | Gln | Leu | Glu | Gly 495 | Gly |
| Cys | Asn | Tyr | Asp 500 | Tyr | Ile | Leu | Val | Phe 505 | Asp | Gly | Pro | Glu | Asn 510 | Asn | Ser |
| Ser | Leu | Ile 515 | Ala | Arg | Val | Cys | Asp 520 | Gly | Phe | Asn | Gly | Ser 525 | Phe | Thr | Ser |
| Thr | Gln 530 | Asn | Phe | Met | Ser | Val 535 | Val | Phe | Ile | Thr | Asp 540 | Gly | Ser | Val | Thr |
| Arg 545 | Arg | Gly | Phe | Gln | Ala 550 | Asp | Tyr | Tyr | Ser | Thr 555 | Pro | Ile | Ser | Thr | Ser 560 |
| Thr | Thr | Ser | Pro | Thr 565 | Thr | Phe | Pro | Ile | Val 570 | Thr | Asp | Trp | Trp | Thr 575 | Thr |
| Pro | Ser | Pro | Glu 580 | Tyr | Thr | Cys | Gly | Gly 585 | Leu | Leu | Thr | Leu | Pro 590 | Tyr | Gly |
| Gln | Phe | Ser 595 | Ser | Pro | Tyr | Tyr | Pro 600 | Gly | Ser | Tyr | Pro | Asn 605 | Asn | Ala | Arg |
| Cys | Leu 610 | Trp | Lys | Ile | Phe | Val 615 | Pro | Ser | Met | Asn | Arg 620 | Val | Thr | Val | Val |
| Phe 625 | Thr | Asp | Val | Gln | Leu 630 | Glu | Gly | Gly | Cys | Asn 635 | Tyr | Asp | Tyr | Ile | Leu 640 |
| Gly | Phe | Asp | Gly | Pro 645 | Glu | Tyr | Asn | Ser | Ser 650 | Leu | Ile | Ala | Arg | Val 655 | Cys |

```
Asp Gly Ser Asn Gly Ser Phe Thr Ser Thr Gln Asn Phe Met Ser Val
            660             665                 670
Val Phe Ile Thr Asp Gly Ser Val Thr Arg Arg Gly Phe Gln Ala Asp
        675             680                 685
Tyr Tyr Ser Thr Pro Ile Arg Thr Ser Thr Thr Pro Pro Thr Thr Phe
        690             695             700
Pro Ile Ile Thr Gly Asn Asp Ser Ser Leu Val Leu Arg Leu Val Asn
705             710             715                 720
Gly Thr Asn Arg Cys Glu Gly Arg Val Glu Ile Leu Tyr Arg Gly Ser
                725             730                 735
Trp Val Pro Cys Ala Asp Asp Ser Trp Asp Ile Asn Asp Ala Asn Val
            740             745                 750
Val Cys Arg Gln Leu Gly Cys Gly Ser Ala Leu Ser Ala Pro Gly Asn
        755             760             765
Ala Trp Phe Gly Gln Gly Ser Gly Leu Ile Val Leu Asp Asp Val Ser
770             775             780
Cys Ser Gly Tyr Glu Ser His Leu Trp Asn Cys Arg His Pro Gly Trp
785             790             795                 800
Leu Val His Asn Cys Arg His Val Glu Asp Ala Gly Val Ile Cys Ser
            805             810                 815
Leu Pro Asp Pro Thr Pro Ser Pro Gly Pro Val Trp Thr Ser Pro Pro
        820             825             830
Phe Val Asn Tyr Thr Cys Gly Gly Phe Leu Thr Gly Leu Ser Gly Gln
        835             840             845
Phe Ser Ser Pro Tyr Tyr Pro Gly Ser Tyr Pro Asn Asn Ala Arg Cys
850             855             860
Leu Trp Asn Ile Glu Val Pro Asn Asn Tyr Arg Val Thr Val Val Phe
865             870             875             880
Arg Asp Val Gln Leu Glu Gly Gly Cys Asn Tyr Asp Tyr Ile Glu Ile
            885             890             895
Phe Asp Gly Pro His His Ser Ser Pro Leu Ile Ala Arg Val Cys Asp
        900             905             910
Gly Ala Met Gly Ser Phe Thr Ser Thr Ser Asn Phe Met Ser Val Arg
        915             920             925
Phe Thr Thr Asp His Ser Val Thr Arg Arg Gly Phe Arg Ala Asp Tyr
930             935             940
Tyr Ser Asp Phe Asp Asn Asn Thr Thr Asn Leu Leu Cys Leu Ser Asn
945             950             955             960
His Met Arg Ala Ser Val Ser Arg Ser Tyr Leu Gln Ser Met Gly Tyr
            965             970             975
Ser Ser Arg Asp Leu Val Ile Pro Gly Trp Asn Val Ser Tyr Gln Cys
            980             985             990
Gln Pro Gln Ile Thr Gln Arg Glu Val Ile Phe Thr Ile Pro Tyr Thr
        995             1000            1005
Gly Cys Gly Thr Thr Lys Gln Ala Asp Asn Glu Thr Ile Asn Tyr Ser
    1010            1015            1020
Asn Phe Leu Lys Ala Ala Val Ser Asn Gly Ile Ile Lys Arg Arg Lys
1025            1030            1035            1040
Asp Leu His Ile His Val Ser Cys Lys Met Leu Gln Asn Thr Trp Val
            1045            1050            1055
Asn Thr Met Tyr Ile Thr Asn Asn Thr Val Glu Ile Gln Glu Val Gln
            1060            1065            1070
Tyr Gly Asn Phe Asp Val Asn Ile Ser Phe Tyr Thr Ser Ser Ser Phe
```

```
                    1075                    1080                    1085
Leu Tyr Pro Val Thr Ser Ser Pro Tyr Tyr Val Asp Leu Asp Gln Asn
        1090                    1095                1100
Leu Tyr Leu Gln Ala Glu Val Leu His Ser Asp Thr Ser Leu Ala Leu
1105                    1110                1115                    1120
Phe Val Asp Thr Cys Val Ala Ser Pro His Pro Asn Asp Phe Ser Ser
                1125                    1130                1135
Leu Thr Tyr Asp Leu Ile Arg Ser Gly Cys Ile Arg Asp Glu Thr Tyr
                1140                1145                1150
Gln Ser Tyr Ser Ser Pro Ser Pro Arg Ile Thr Arg Phe Lys Phe Ser
            1155                1160                1165
Ser Phe His Phe Leu Asn Arg Phe Pro Ser Val Tyr Leu Gln Cys Lys
        1170                1175                1180
Leu Val Val Cys Arg Ala Asn Asp Val Ser Ser Arg Cys Tyr Arg Gly
1185                1190                    1195                1200
Cys Val Val Arg Ser Lys Arg Asp Val Gly Ser Tyr Gln Glu Lys Val
                1205                1210                    1215
Asp Val Val Leu Gly Pro Ile Gln Leu Gln Ser Pro Ser Lys Glu Lys
                    1220                1225                1230
Arg Ser Leu Asp Leu Ala Val Ala Asp Val Glu Lys Pro Ala Ser Ser
            1235                1240                    1245
Gln Glu Val Tyr Pro Thr Ala Ala Ile Phe Gly Gly Val Phe Leu Ala
1250                    1255                1260
Leu Val Val Ala Val Ala Ala Phe Thr Leu Gly Arg Lys Thr Arg Thr
1265                1270                1275                    1280
Ala Arg Gly Gln Pro Pro Ser Thr Lys Met
            1285                1290
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (vi) ORIGINAL SOURCE:
        (A) ORGANISM: Rattus rattus (xi) SEQUENCE DESCRIPTION: SEQ ID NO:3:

GGACAGAATT CGNGGNAA Y T A Y GGN- GA Y TG    30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Rattus rattus ( x i ) SEQUENCE DESCRIPTION: SEQ ID NO:4:

GATCCACTCG AGNGA Y TTNA CNGANGGCCA    30

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:5:

Ser Leu Gly Gly Asn Tyr Gly Asp Cys
    1                   5

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Trp Pro Ser Val Lys Ser Gln
    1               5